US011992029B2

(12) United States Patent
Peterson

(10) Patent No.: US 11,992,029 B2
(45) Date of Patent: May 28, 2024

(54) METHOD FOR FORMING CELL-BASED-MEAT FIBERS

(71) Applicant: Upside Foods, Inc., Berkeley, CA (US)

(72) Inventor: Mark Peterson, Oakland, CA (US)

(73) Assignee: Upside Foods, Inc., Berkeley, CA (US)

( * ) Notice: Subject to any disclaimer, the term of this patent is extended or adjusted under 35 U.S.C. 154(b) by 0 days.

(21) Appl. No.: 18/045,704

(22) Filed: Oct. 11, 2022

(65) Prior Publication Data

US 2024/0114921 A1 Apr. 11, 2024

(51) Int. Cl.
*A23J 3/22* (2006.01)
*A23J 3/06* (2006.01)
*A23J 3/26* (2006.01)
*A23J 3/28* (2006.01)

(52) U.S. Cl.
CPC .................. *A23J 3/227* (2013.01); *A23J 3/06* (2013.01); *A23J 3/26* (2013.01); *A23J 3/28* (2013.01)

(58) Field of Classification Search
CPC .................................. A23J 3/227; A23J 3/26
See application file for complete search history.

(56) References Cited

U.S. PATENT DOCUMENTS

| 6,323,145 B1 | 11/2001 | Popper |
| 2010/0136201 A1 | 6/2010 | Bigeard et al. |
| 2021/0235733 A1 | 8/2021 | Kayser et al. |

FOREIGN PATENT DOCUMENTS

| WO | WO 2022/047263 | * | 3/2022 |
| WO | WO 2022/157584 A2 | | 7/2022 |

OTHER PUBLICATIONS

No Spoon Necessary, "How to Grind Your Own Burger Meat", https://www.nospoonnecessary.com/grind-your-own-burger-meat/, 2019, downloaded Jul. 9, 2023. (Year: 2019).*
Snappy Living, "23 Ingredient to Improve Your Burger Recipe", https://snappyliving.com/better-hamburgers-with-mix-in-ingredients/, 2019, downloaded Jul. 8, 2023. (Year: 2019).*
Hong et al. (WO 2022/019688—Clarivate translation) (Year: 2022).*
Tsai et al., "Sectioned and Formed Product Made from Emulsion-Coated Pork Tissue", Journal of Food Science, vol. 47, (1982), pp. 1080-1082. (Year: 1982).*
Finedining Lovers, "Braided Pork Filet with Balsamic Vinegar", FineDining Lovers, Mar. 2012, https://www.finedininglovers.com/recipes/main-course/braided-pork-filet-balsamic-vinegar, downloaded Oct. 11, 2023. (Year: 2012).*
Chen et al., "Sensory, Instrumental Texture Profile and Cooking Properties of Restructured Beef Steaks Made with Various Binders", J. Food Sci., vol. 56, No. 6, (1991), pp. 1457-1450. (Year: 1991).*

(Continued)

*Primary Examiner* — Elizabeth Gwartney
(74) *Attorney, Agent, or Firm* — Keller Preece PLLC

(57) ABSTRACT

This disclosure describes methods for forming cell-based-meat products that mimic cuts of slaughtered meat. Generally, the disclosed method comprises forming a cell mass into primary structures, including fibers and/or sheets. A toughening agent is applied to the exterior surfaces of the primary structures, and the primary structures are arranged to mimic structures in a target slaughtered meat. The toughening agent creates a textural contrast that, during consumption, is like the textural contrast experienced when biting through bundles of meat fibers in slaughtered meat.

20 Claims, 17 Drawing Sheets

(56) References Cited

OTHER PUBLICATIONS

Dr. - Ing. Valerie Pietsch; Youtube.com; "Introduction into Meat Analog Extrusion"; date downloaded Dec. 15, 2022; https://www.youtube.com/watch?v=oyGiwqAtCjs&ab_channel=MaJaTFS.
Donna Berry; Meatpoultry.com; "The role of extrusion in plant-based meat processing"; Date downloaded Dec. 15, 2022; https://www.meatpoultry.com/articles/23531-the-role-of-extrusion-in-plant-based-meat-processing.
B.L. Dekkers et al. Structuring processes for meat analogues. Trends in Food Science & Technology 81 (2018) 25-36.
MacQueen, L.A., Alver, C.G., Chantre, C.O. et al. Muscle tissue engineering in fibrous gelatin: implications for meat analogs. npj Sci Food 3, 20 (2019). https://doi.org/10.1038/s41538-019-0054-8.
International Search Report & Written Opinion as received in PCT/US 22/77986 dated Mar. 3, 2023.

* cited by examiner

METHOD FOR FORMING CELL-BASED-MEAT FIBERS

BACKGROUND

As the world's population continues to grow, cell-based or cultured meat products for consumption have emerged as an attractive alternative (or supplement) to conventional meat from animals. For instance, cell-based, cultivated, or cultured meat represents a technology that could address the specific dietary needs of humans. Cell-based meat products can be prepared from a combination of cultivated adherent and suspension cells derived from a non-human animal. Because the cells for cell-based meat are made in a food cultivation facility, cell masses are often formed and shaped to mimic familiar forms of conventional meat.

In addition to addressing dietary needs, cell-based-meat products help alleviate several drawbacks linked to conventional meat products for humans, livestock, and the environment. For instance, conventional meat production involves controversial practices associated with animal husbandry, slaughter, and harvesting. Other drawbacks associated with harvested or slaughtered meat production include low conversion of caloric input to edible nutrients, microbial contamination of the product, emergence and propagation of veterinary and zoonotic diseases, relative natural resource requirements, and resultant industrial pollutants, such as greenhouse gas emissions and nitrogen waste streams.

Despite advances in creating cell-based-meat products, existing methods or systems for cultivating and processing cell-based-meat products face several shortcomings, such as challenges or failures to mimic the textures and flavors of slaughtered or harvested meat. Existing methods or systems often produce cell-based-meat products with undesirable textures. For example, existing systems often form cell-based-meat products that lack structure and are more similar to ground or processed meat products than highly ordered cuts of conventional meat, such as a steak. Furthermore, existing cell-based-meat products are often formless and lack the fibrous structure, i.e., the grain, found in conventionally slaughtered meat.

These, along with additional problems and issues are present in existing methods for cultivating cell-based-meat products

BRIEF SUMMARY

This disclosure generally describes methods and apparatuses for applying a toughening agent to fiber-shaped cell-based meat to toughen and define fiber-like (or sheet-like) boundaries and further arranging the toughened meat fibers in a cell-based-meat product to mimic the fibers or other structures of a target slaughtered meat. To illustrate, in some cases, the disclosed method forms a cell mass into primary structures, such as fibers or sheets of cellular meat tissue. The disclosed method further comprises applying a toughening agent to the primary structures—before combining and ordering the primary structures—to define boundaries between (or among) such primary structure. The resulting cell-based-meat product is made of meat fibers or sheets having toughened boundaries that contribute to a fibrous texture characteristic of a target slaughtered meat. In some cases, for instance, the method mimics particular cuts of meat comprising muscle fibers organized into bundles (e.g., beef, poultry) or flakes (e.g., fish).

Additional features and advantages of one or more embodiments of the present disclosure will be set forth in the description that follows.

BRIEF DESCRIPTION OF THE DRAWINGS

Various embodiments will be described and explained with additional specificity and detail through the use of the accompanying drawings, which are summarized below.

DETAILED DESCRIPTION

Figure 1:
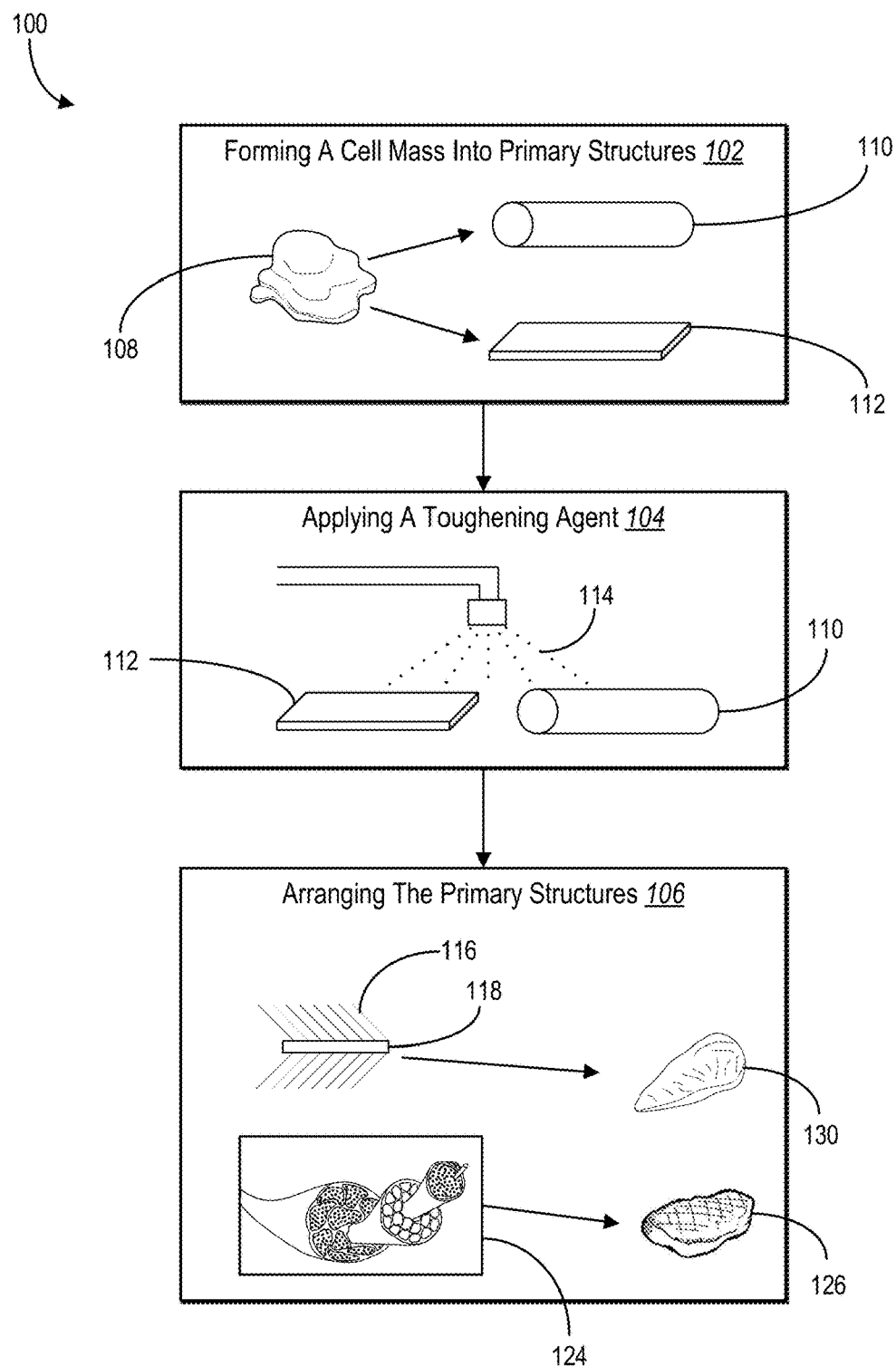
FIG. 1 illustrates an overview diagram of arranging primary structures to mimic structures in a target slaughtered meat in accordance with one or more embodiments of the present disclosure.

This disclosure describes one or more embodiments of a method for forming meat structures having toughened boundaries and combining the structures to form a cell-based meat having a robust fibrous architecture. Generally, the disclosed method comprises forming animal cells into structures, including fibers and sheets. A toughening agent is applied to the outside surface of the structures and one or more structures are combined in a way to mimic the muscular structure of a target meat. For example, toughened fibers and sheets may be arranged within a mold having a shape of a target cut of meat to mimic the muscular architecture of the target cut of meat.

To illustrate, in some implementations, the disclosed method comprises forming a cell mass into primary structures. The disclosed method further includes applying a toughening agent to exterior surfaces of the primary structures and arranging the primary structures comprising the toughened exterior surfaces to mimic structures in a target slaughtered meat. For example, the disclosed method may comprise arranging primary structures in a mold to mimic structures in a target slaughtered meat.

As just noted, in some cases, the disclosed method comprises forming a cell mass into primary structures.

Generally, the primary structures are the basic components of the organized cell-based-meat product architecture. For example, primary structures may comprise fibers or sheets formed using various methods. To illustrate, the disclosed method may include forming the primary structures by filling containers with a cell mass or by extruding the cell mass.

In at least one example, the disclosed method comprises forming a cell mass into primary fibers and applying a toughening agent to exterior surfaces of the primary fibers. The primary fibers are woven to form a secondary fiber comprising interwoven primary fibers. Additionally, in some cases, secondary fibers are woven to form a tertiary fibers. By interweaving different structure types, the method can form complex, fibrous structures that mimic natural, muscle fibers of a target slaughtered meat.

As noted above, in some embodiments, the disclosed method further comprises applying a toughening agent to the exterior surfaces of primary structures or other structures formed from a cell mass. Toughening agents alter the exterior surfaces of the primary (or other type of) structures to create textural boundaries. The application of toughening agents creates a textural contrast between the exterior surface of a primary (or other type of) structure and the internal portion of the primary structure. This textural contrast provides variable resistance to chewing forces, which may provide a chewing experience that mimics the experience of chewing conventional, slaughtered meat, which has textural contrasts provided by muscle fibers' structure, directionality, and supporting fat and tissue.

In addition to applying a toughening agent, the primary (or other type of) structures comprising the toughened exterior surfaces are arranged to mimic structures in a target slaughtered meat. To illustrate, primary structures can be organized to mimic the arrangement of muscle fiber bundles in a conventional cut of meat, such as parallel fibers, e.g., a grain, stemming from a primary fiber mimicking connecting tissue in a chicken breast or fibers arranged like spokes around a center point to mimic a cut of ham. Additionally, or alternatively, sheets of animal cells can be layered to mimic layers found in fish meat.

As indicated above, the disclosed method provides several benefits relative to existing methods for forming cell-based-meat products. In particular, the disclosed method forms fiber-like structures or layers with improved structure and texture relative to existing methods. By applying a toughening agent to the exterior surfaces of primary (or other type of) structures from a cell mass, the disclosed method creates a textural contrast within individual primary structures, wherein the textural contrast is perceptible when chewed, cut, or otherwise incised. Furthermore, in some cases, the primary structures are arranged to mimic the unique architecture of muscle fiber bundles found in various cuts of conventional meat, such as sliced ham or chicken breast or sliced salmon. In particular, the primary, secondary, and tertiary structures may be arranged to mimic a grain of a target cut of meat. The toughened boundaries running through the resulting cell-based-meat product provide a variable tactile resistance to teeth during consumption unlike existing cell-based-meat products. The tactile resistance provided by the toughened boundaries mimics resistance provided by interfacing muscle fiber bundles in conventional meat, such as the fiber bundles of target cuts of meat. Accordingly, the disclosed method forms cell-based-meat products having improved texture, structure, and form relative to existing methods.

As illustrated by the foregoing discussion, the present disclosure utilizes a variety of terms to describe features and advantages of the disclosed method. Additional detail is now provided regarding the meaning of such terms. As used herein, the term "cells" (or "animal cells") refers to cells that form meat. Generally, animal cells may comprise at least one of muscle cells, muscle progenitor cells, or muscle support cells. In particular, animal cells may comprise different cell types, such as one or more of myoblasts, mesangioblasts, myofibroblasts, mesenchymal stem cells, hepatocytes, fibroblasts, pericytes, adipocytes, epithelial, chondrocytes, osteoblasts, osteoclasts, pluripotent cells, somatic stem cells, endothelial cells, or other similar cell types. Furthermore, cells may comprise different types of progenitor cells, including myogenic progeny and progenitors, adipogenic progeny or progenitors, mesenchymal progeny or progenitors, or other types of progenitor cells.

As used herein, the term "cell mass" refers to a tissue or mass of animal cells. A cell mass includes cells of cultivated meat gathered into a collective mass. Such a cell mass may nevertheless be raw or uncooked. In some embodiments, the cell mass is comestible. Additionally, a cell mass can include grown cells that have been nourished by a growth medium to grow during a formation period within a cultivator. In some examples, a cell mass is grown from cells attached to a substrate in an adherent reactor and/or grown from cells floating in liquid in a suspension reactor.

As further used herein, the term "primary structure" refers to a first order basic shape or structure of cells that makes up a larger structure. In particular, a primary structure comprises a basic shape of a cell mass. For example, a primary structure may comprise a primary sheet having a flattened shape or a primary fiber.

Relatedly, as used herein, the term "secondary structure" refers to a second order shape or structure of cells made up of component primary structures. In particular, a secondary structure comprises a structure made of arranged primary structures. For example, a secondary structure can comprise a fiber composed of intertwined primary fibers. In another example, a secondary structure comprises a tube made of a primary sheet wrapped around a bundle of primary fibers.

Relatedly, as used herein, the term "tertiary structure" refers to a third order shape or structure of cells made up of component primary and/or secondary structures. In particular, a tertiary structure comprises a structure made of arranged primary and/or secondary structures. For example, a tertiary structure can comprise a fiber composed of intertwined secondary fibers. In another example, a tertiary structure comprises a tube made of a primary sheet wrapped around a bundle of secondary fibers. Quaternary and other higher ordered structures readily flow from the logic of this description and their use is expressly contemplated herein.

As used herein, a "primary fiber" refers to a primary structure of cells organized in a fibril structure, such as a thread or filament of meat. In particular, a primary fiber comprises a portion of cell mass formed into a fiber or a fiber-like shape. Relatedly, as used herein, the term "secondary fiber" refers to an ordered fiber comprised of primary structures. In particular, a secondary fiber comprises an elongated structure made up of primary fibers and/or other primary structures. For example, a secondary fiber may comprise interwoven primary fibers encapsulated in a primary sheet. Related, as used herein, the term "tertiary fiber" refers to an ordered fiber comprised of primary and/or secondary structures. In particular, a tertiary fiber may comprise an elongated structure made up of primary fibers, second fibers, and/or other primary and secondary structures. Quaternary fibers and other higher ordered fibers readily flow from the logic of this description and their use is expressly contemplated herein.

As used herein, the term "grain" refers to a direction that fibers run within a piece of meat or cell-based-meat product. Muscle fibers within meat often run parallel to one another. The grain refers to the direction that long muscle fibers run down and through an entire piece of meat. In one example, primary structures including sheets and fibers are arranged to run substantially parallel to one another to create a grain having a similar structure to the grain found in slaughtered meat.

As used herein, the term "toughening agent" refers to a substance used to toughen a material. In particular, a toughening agent can include a biochemical substance that strengthens or hardens an exterior surface of a primary structure. In some embodiments, a toughening agent increases a material's resistance to crushing forces and/or incising forces. For example, a toughening agent can comprise compounds, such as gelatin or collagen. In some implementations, toughening agents comprise cells, such as fibroblasts or adipocytes cultivated and/or processed such that they provide strength or hardness to an exterior surface of a structure. In another example, toughening agents comprise lipids, including cooking oils, shortening, and others. Toughening agents may also be other carbohydrate-based texturizers, such as corn starch, amylose, transglutimase, etc. Toughening agents may also comprise a combination of the above-mentioned examples. In one example, a toughening agent increases the bite force required to penetrate softer material deeper than the toughening agent. A toughening agent may also provide a degree of at least temporary stickiness to facilitate the adhesion of two or more substances exposed to a toughening agent. Furthermore, in some examples, a toughening agent may be customized for resistance to crushing forces and stickiness. Additionally, two or more different toughening agents may be used on any given structure.

As used herein, the term "exterior surface" refers to the outside surface of a primary structure or other higher ordered structures. In particular, an exterior surface comprises an outside surface of a primary structure (or other structure) that is exposed to external substances, such as air or adjacent structures. In some examples, a toughening agent is applied to exterior surfaces of a primary (or other type of) structure.

As used herein, the term "target slaughtered meat" refers to a slaughtered meat with a structure targeted for imitation by a cell-based-meat product. In particular, a target slaughtered meat comprises muscle fiber bundles, typically organized into grains, and/or other muscle fiber structures organized in a particular way specific to the given slaughtered meat. For example, a target slaughtered meat may include red meat, poultry, or seafood. In some implementations, target slaughtered meat comprises processed slaughtered meat products like ham.

As used herein, the term "mold" refers to a hollow container used to give shape to a material. In particular, a mold includes a container with a depression having a shape of a target meat product. More specifically, a mold may comprise a food-safe container in the shape of a target slaughtered meat. For example, a mold may comprise a container in the shape of a beef steak, a chicken breast, a fish fillet, a crab claw, a ham, or another cut of meat.

Additional detail will now be provided regarding the disclosed method in relation to illustrative figures portraying example embodiments and implementations of the disclosed methods. FIG. 1 illustrates an overview of arranging primary structures having toughened exterior surfaces to mimic a muscular architecture of a target slaughtered meat. By way of overview, FIG. 1 illustrates a series of acts 100 comprising an act 102 of forming a cell mass into primary structures, an act 104 of applying a toughening agent, and an act 106 of arranging the primary structures.

Figure 3:
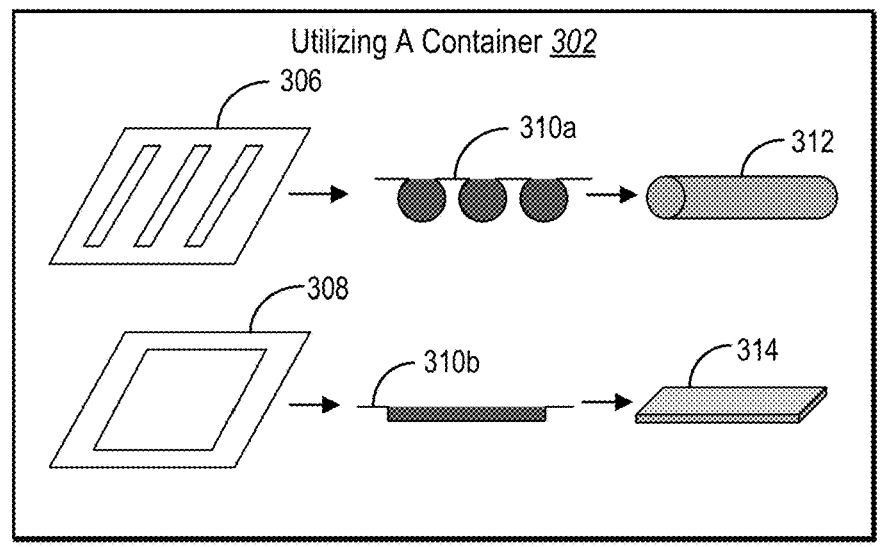
FIG. 3 illustrates forming primary structures in accordance with one or more embodiments of the present disclosure.
Figure 3:
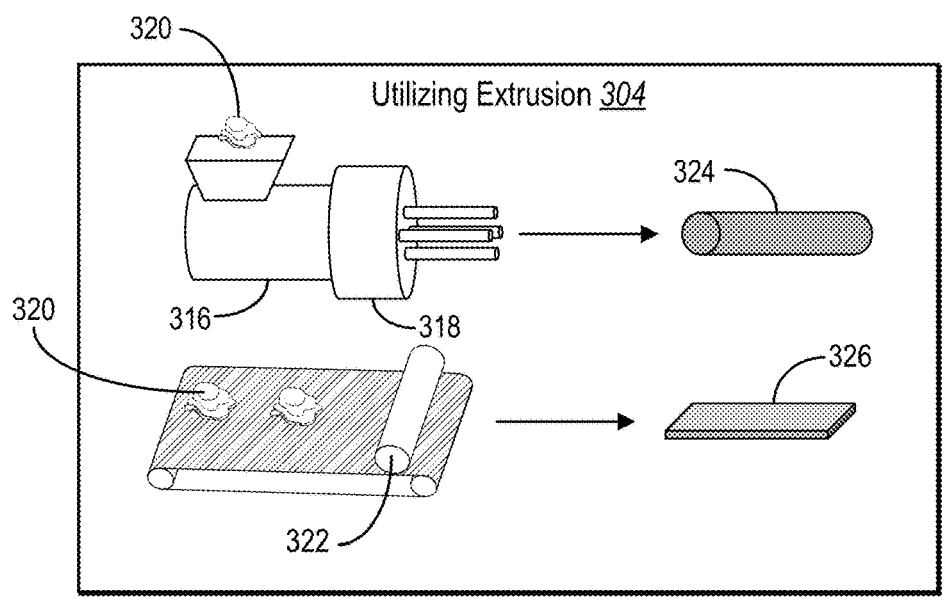

FIG. 1 illustrates the act 102 of forming a cell mass into primary structures. As illustrated, the act 102 comprises forming a cell mass 108 into primary structures comprising a primary fiber 110 and/or a primary sheet 112. Generally, the cell mass can comprise cells of different cell types including myocytes, adipocytes, or fibroblasts. Each of the primary structures may comprise cells of one or more cell type. FIG. 3 illustrates example methods for forming the primary fiber 110 and the primary sheet 112 in accordance with one or more embodiments. Furthermore, FIGS. 14A-14D and the corresponding paragraphs detail cultivating cells to form the cell mass in accordance with one or more embodiments.

Figure 2:
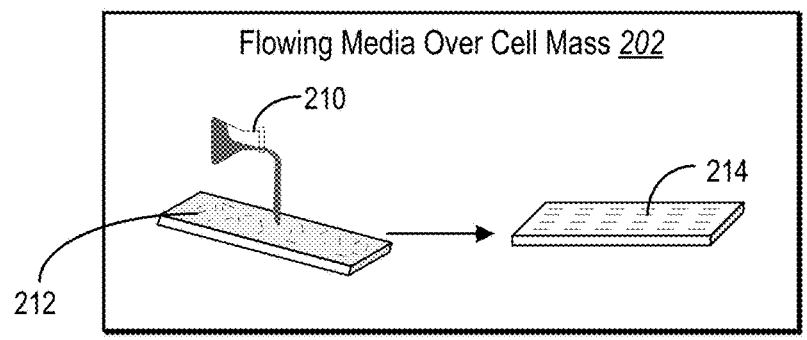
FIG. 2 illustrates an overview diagram of arranging proto-fibers in a cell mass in accordance with one or more embodiments of the present disclosure.
Figure 2:
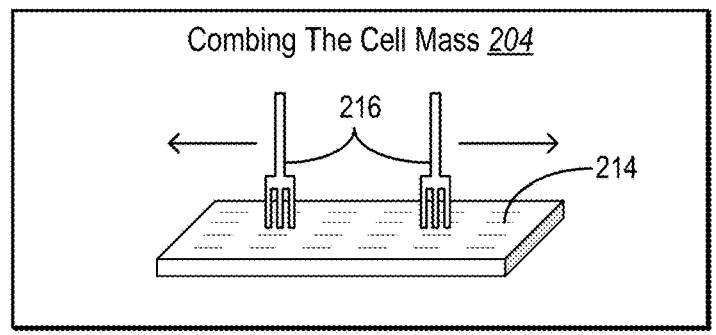
Figure 2:
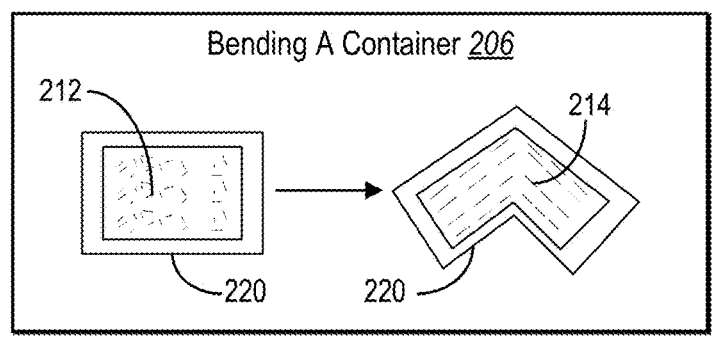
Figure 2:
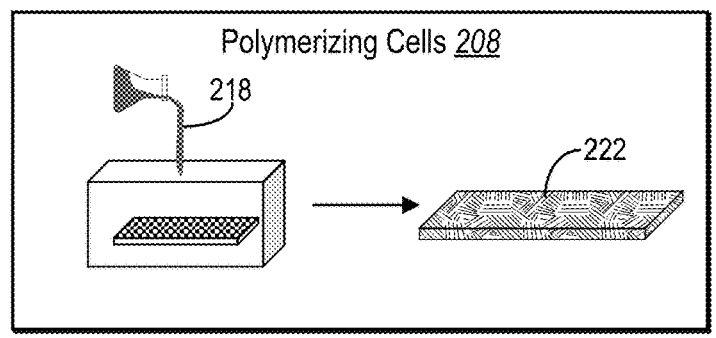

In some implementations, the series of acts 100 comprises an optional act of organizing proto-fibers in the cell mass. The optional act may be performed prior to or during the act 102 of forming the cell mass into primary structures. Generally, proto-fibers comprise filaments within a cell mass. The optional act may include arranging the proto-fibers to further mimic alignment of muscle cells in conventional meat. FIG. 2 and the corresponding discussion further detail organizing proto-fibers in the cell mass in accordance with one or more embodiments.

Figure 4:
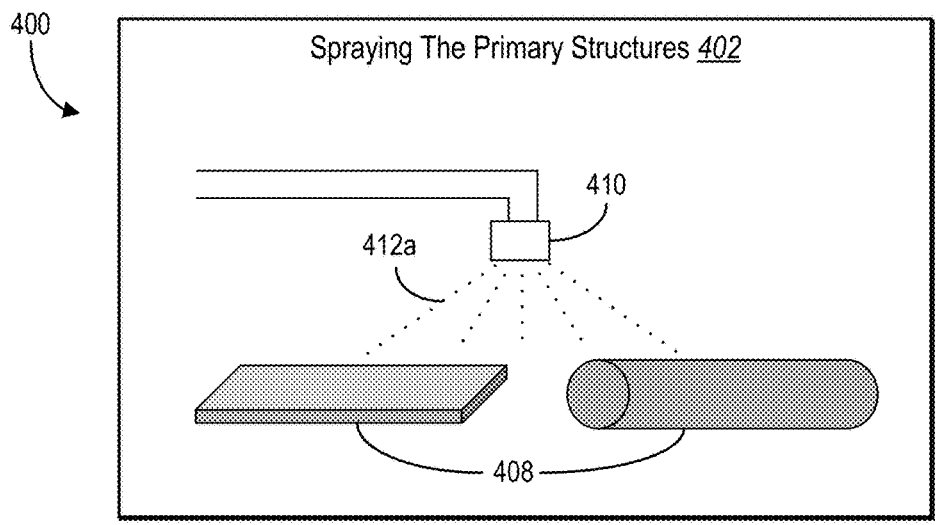
FIG. 4 illustrates applying a toughening agent in accordance with one or more embodiments of the present disclosure.
Figure 4:
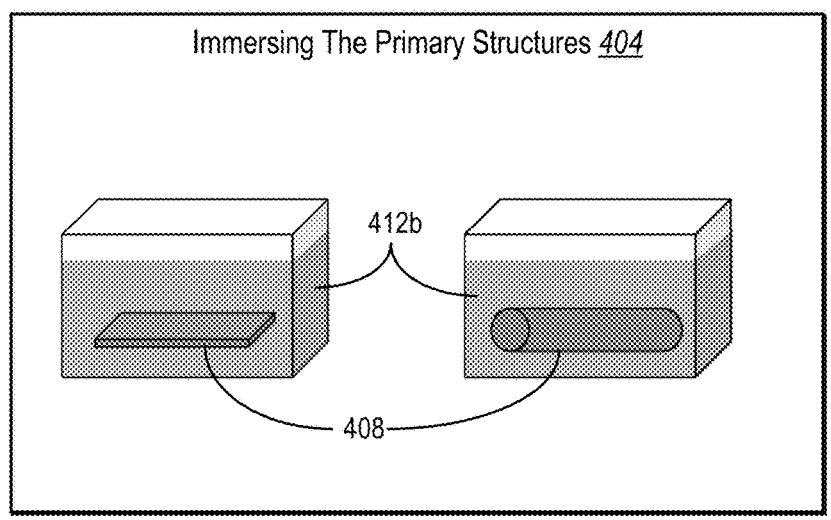
Figure 4:
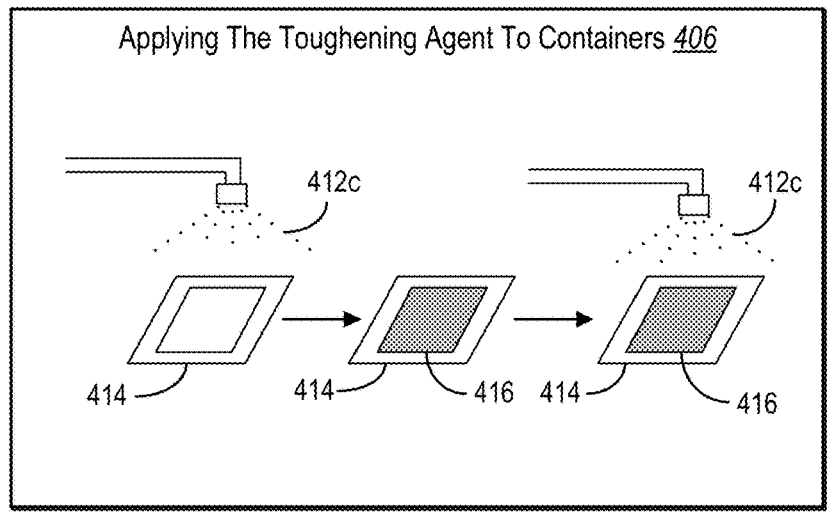

As further shown in FIG. 1, the series of acts 100 further includes the act 104 of applying a toughening agent. More specifically, the act 104 comprises applying a toughening agent to exterior surfaces of the primary structures. As illustrated, the act 104 comprises applying a toughening agent 114 onto exterior surfaces of the primary fiber 110 and/or the primary sheet 112. Generally, the toughening agent 114 toughens or strengthens the exterior surfaces of the primary structures against incision or incision-like physical forces relative to interior portions of the primary structures, wherein a bite force required to incise the primary structure has a value that varies between the exterior and interior portions of the primary structures. FIG. 4 and the corresponding paragraphs provide examples methods for applying the toughening agent 114 to primary structures in accordance with one or more embodiments.

As further illustrated in FIG. 1, the disclosed method includes the act 106 of arranging the primary structures. The act 106 comprises arranging the primary structures comprising the toughened exterior surfaces to mimic structures in a target slaughtered meat. In some implementations, primary structures of the same shape are organized to form a final cell-based meat product. For example, primary fibers can be combined in a hierarchical fashion to mimic the progressive grouping of muscle fibers and grains found in conventional meat. For example, conventional meat is made up of individual muscle fibers or muscle cells having myorfibrils, which are bundled into larger fascicles. As illustrated by the hierarchical structure 124 of a resulting cell-based-meat product, primary fibers can be bundled together to form secondary fibers which are, in turn, bundled to form tertiary fibers. The hierarchical structure 124 can be cut "against the grain" to form a cell-based-meat product with a similar structure and texture as, for example, a beef steak 126. Other target slaughtered meats and corresponding processes are described below.

Figure 5:
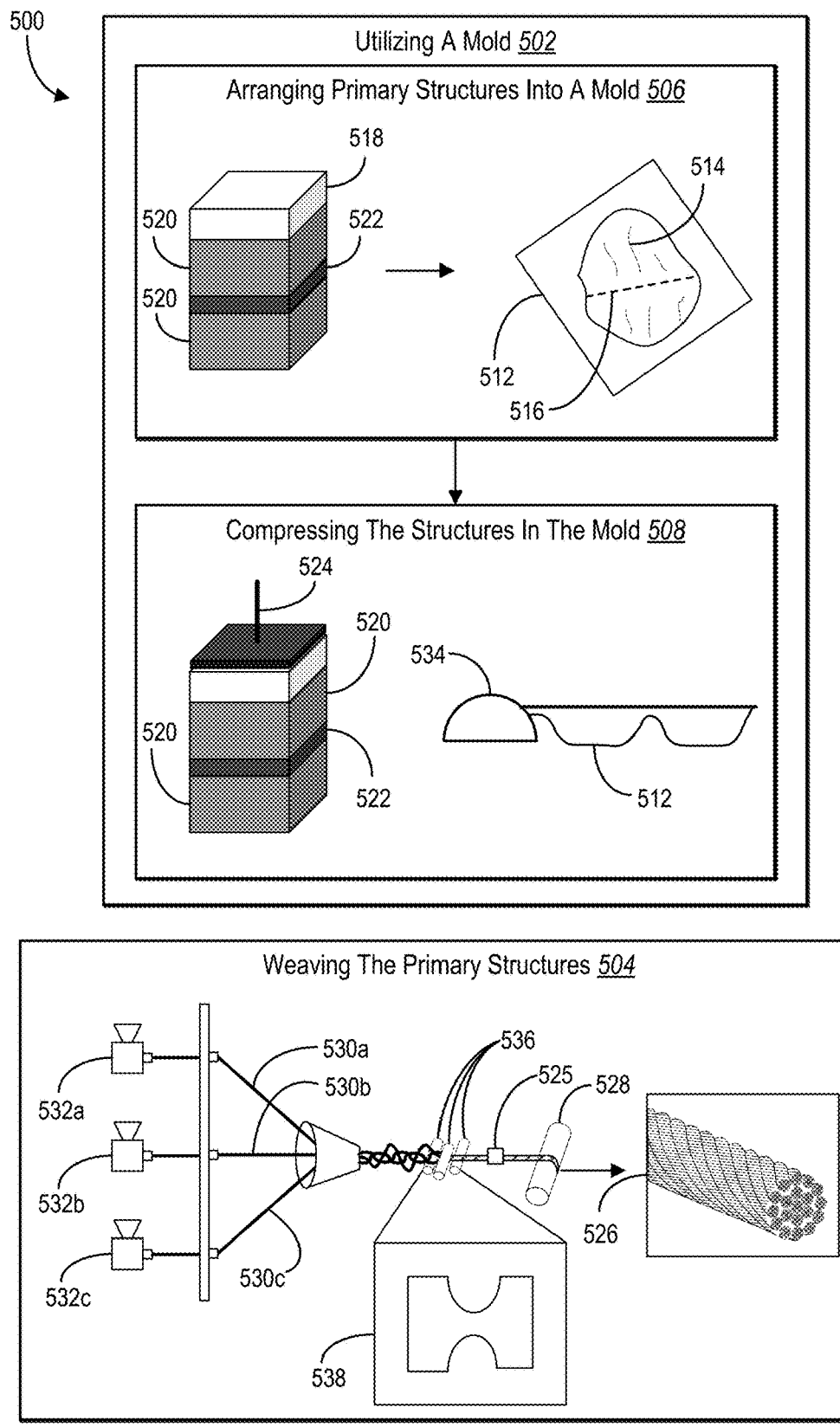
FIG. 5 illustrates arranging primary structures in accordance with one or more embodiments of the present disclosure.

In some implementations, the act 106 comprises combining primary structures of different shapes to form a cell-based meat product. To illustrate, primary fibers 116 may be combined with a primary sheet 118 (or another primary fiber) to form a cell-based-meat product 130 that mimics a chicken breast. FIG. 5 and the corresponding paragraphs detail example methods for arranging primary structures in accordance with one or more embodiments.

As mentioned, in some implementations, the disclosed method comprises organizing proto-fibers in a cell mass. FIG. 2 illustrates example methods for organizing proto-fibers in accordance with one or more embodiments. By way of overview, FIG. 2 illustrates a method 202 of flowing media over a cell mass, a method 204 of combing the cell mass, a method 206 of bending a container, and a method 208 of polymerizing the cells. As described below, each of the methods 202, 204, 206, and 206 can be used to organize proto-fibers in a cell mass.

Aligning proto-fibers in the cell mass and/or the primary structures improves the texture of the cell-based-meat product. A cell mass is comprised of cells comprising filaments that may be directionally oriented. For example, the filaments may comprise myo sin heavy chains (MyHC) that are randomly oriented within a freshly grown and harvested cell mass. In another example, filaments refer to myofibrils or bundles of protein filaments within muscle or animal cells. The disclosed method may comprise enhancing the form and texture of primary structures by organizing the proto-fibers. To illustrate, proto-fibers may be aligned along the length of a primary fiber to mimic the orientation of myofibrils found in conventional muscle tissue. This additional organization of proto-fibers within the primary structures enhances alignment and strengthens individual primary structures, which in turn improves the texture of the cell-based-meat product.

As indicated above, the disclosed method comprises organizing proto-fibers in a cell mass prior to or during forming the cell mass into primary structures. The methods illustrated in FIG. 2 may be performed prior to and/or during the formation of primary structures. For example, in some implementations, the methods illustrated in FIG. 2 are performed on a cell mass that has just been grown and harvested. In some implementations, the illustrated proto-fiber organizing methods are performed during primary structure formation. For example, the methods may be performed while the cell mass is in a container or in the process of extrusion.

FIG. 2 illustrates the method 202 of flowing media over a cell mass. Generally, the method 202 comprises flowing a media 210 over a cell mass having unorganized proto-fibers 212. The friction between fluid particles in the media 210 and cells within the cell mass cause the cells to orient in the direction of flow. As illustrated, the resulting cell mass comprises aligned proto-fibers 214. The media 210 may comprise any sort of cellular media or fluid buffer. For example, in some implementations, the media 210 comprises differentiation media that stimulates cells within the cell mass to differentiate, whereby proto-fiber growth is increased. In other examples, the media 210 comprises a cellular growth media, a wash buffer, an enrichment media, or another solution.

As further illustrated in FIG. 2, proto-fibers may be arranged by the method 204 of combing the cell mass. The method 204 comprises physically combing the cell mass to orient proto-fibers in the cell mass along the direction of the combing. For example, the method 204 comprises combing the cell mass with tines 216 to orient the aligned proto-fibers 214 along the direction in which the tines 216 were pulled.

In some embodiments, the method 204 is performed on a cell mass prior to primary structure formation. In some embodiments, the method 204 is performed by combing the cell mass within a container or combing a cell mass as it leaves an extruder. For example, the tines 216 may be attached to the interior and/or a die of an extruder such that proto-fibers are organized during primary structure formation. In another example, the proto-fibers are aligned parallel to the length of a container's depression, for example, by using penetrating brushes to comb along the length of the container.

In addition or in the alternative to combining a cell mass, FIG. 2 illustrates the method 206 of bending a container. Generally, the method 206 aligns proto-fibers by stretching the cell mass to induce hypertrophy and align proto-fibers. In some examples, the cell mass is placed in a container 220. Bending or rolling the container 220 creates friction between the surface of the container 220 that is in contact with the cell mass and the cell mass. The friction may cause proto-fibers to orient in a direction perpendicular to the crease of the bend. Furthermore, bending or folding the container 220 may stress the cells in the cell mass, which induces hypertrophy of the cells. The container 220 may comprise a container used for forming the primary structures or a separate container. For example, the container 220 illustrated in FIG. 2 comprises a container for forming a primary sheet.

As further illustrated in FIG. 2, proto-fibers may be arranged by the method 208 of polymerizing the cells. More specifically, the method 208 comprises polymerizing myofibrils or the component proteins of myofibrils. For example, the method 208 may polymerize actin or myosin filaments, which form the myofibrils of the animal cells. In some implementations, the method 208 can be performed by adding a polymerization solution 218 to a cell mass. In some embodiments, the polymerization solution 218 comprises a solution having high ionic strength. For example, the ionic strength of the polymerization solution 218 may be similar to the ionic strength of biological fluids. As a result of polymerization of proto-fibers 222, the cells within the cell mass interconnect to form a 3D network.

In further embodiments, two or more of the proto-fiber alignment methods depicted in FIG. 2 are combined to further enhance proto-fiber alignment, length, and/or volume in a primary structure.

As described previously, the disclosed method may form primary structures by various means. In accordance with one or more embodiments, FIG. 3 illustrates example methods 300 for forming primary structures. By way of overview, the disclosed method forms primary structures by method 302 utilizing a container or by method 304 of utilizing extrusion.

In some embodiments, as part of forming the primary structures, the disclosed method comprises mixing the cell mass with a binding agent. Generally, mixing the cell mass with a binding agent facilitates the formation of elongated fibers and/or the formation of intact sheets. More specifically, binding agents draw cells within the cell mass together to form a cohesive whole. Binding agents aid in primary structure formation by fortifying the primary structures during and after formation. Binding agents may include transglutaminase, modified starches, carrageenan, soluble and insoluble fibers, gelatin, sodium caseinate, wheat gluten, dry milk, protein, and others. Additionally, or alternatively, binding agents include gums, such as guar or xanthan gum. Binding agents may be added to the cell mass before utilizing either or both of the method 302 and the method 304 illustrated in FIG. 3.

As mentioned previously, the cell mass used to form the primary structures illustrated in FIG. 3 may comprise cells of the same or different cell types. For example, a cell mass may generally comprise adherent cells and/or suspension cells. Adherent cells are grown attached to a substrate, while suspension cells are grown in an agitated growth medium. In some implementations, cells grown in suspension are dewetted to meet a target moisture content prior to primary structure formation. Adherent cells and suspension cells can be further categorized into different cell types. Example cell types that may be grown as adherent or suspension cultures include, but are not limited to, myoblast, adipocytes, fibroblasts, and others. In some implementations a single primary structure is made up of cells of a single cell type. In other implementations, a single primary structure comprises a mixture of cells of various cell types. FIGS. 14A-14D and the corresponding description below further detail methods for growing and processing different types of cells in accordance with one or more embodiments.

As illustrated in FIG. 3, the methods 300 includes the method 302 of utilizing a container. In some implementations, the method 302 comprises utilizing more than one container. Generally, the method 302 comprises forming a cell mass into primary structures by adding the cell mass to containers having shapes of the primary structures. As shown, the disclosed method may utilize a fiber container 306 or a sheet container 308 for forming a primary fiber 312 and a primary sheet 314, respectively. The fiber container 306 comprises a tray having indentations or depressions having the shape of the primary fiber. The disclosed method comprises filling the depressions of the fiber container 306 with a cell mass 310a. Similarly, the sheet container 308 has a depression in the shape of a primary sheet, which is filled with a cell mass 310b. Although the following paragraphs describe using the fiber container 306 and the sheet container 308 to form primary structures, each can be used independent of one another.

In some implementations, the disclosed method comprises removing air from the container to facilitate forming. As part of one such air-removing process, in some cases, the disclosed method comprises pressing the cell mass into the container. In some implementations, the cell mass is mechanically forced into the depressions using an applicator. For example, an applicator may comprise a tool resembling a putty knife. The disclosed method comprises pressing the cell mass into the depressions using the blade of the applicator. The applicator simultaneously removes excess cell mass from the surface of the container.

In addition, or in the alternative to pressing a cell mass into a container, the disclosed method forces the cell mass into the depressions of the containers by vacuum sealing the cell mass and the container. Vacuum sealing both removes air bubbles from within the cell mass and pulls the cell mass into the container's shape. For example, in some implementations, a film (e.g., a polycarbonate sheet) is placed on the fiber container 306 or the sheet container 308 after adding the cell mass 310b and/or the cell mass 310b to the respective containers. The disclosed method comprises vacuuming the container and the cell mass.

After pressing or forcing the cell mass into respective containers, the cell mass 310a is allowed to set in the fiber container 306. Additionally, or alternatively, the cell mass 310b is allowed to set in the sheet container 308. In some implementations, and as described in greater detail below with respect to FIG. 4, toughening agent is applied to the empty container, the cell mass 310a, and/or the cell mass 310b while in their respective containers. When activated, the toughening agent strengthens the exterior surfaces of the cell mass such that the primary fiber 312 and/or the primary sheet 314 can be removed from the fiber container 306 and the sheet container 308, respectively, while retaining their shapes. In some implementations, the primary fiber 312 and/or the primary sheet 314 are not removed from their respective containers until the toughening agent has been activated, set, or cured.

In some implementations, the cell mass 310a or 310b is allowed to set in the fiber container 306 or the sheet container 308 for a threshold setting time period. During the threshold setting time period, the cell mass 310a or 310b may begin to retain their shape by losing moisture or simply allowing enough time for the binding agents to work and solidify bonds between cells. After the threshold setting time period, the primary fiber 312 or the primary sheet 314 is removed from the fiber container 306 or the sheet container 308, respectively.

The containers used in the method 302 can have depressions of various shapes and sizes. For example, the fiber container 306 can have thicker and longer depressions of a size like angel hair pasta noodles or thinner and shorter depressions of a size similar to crab meat fibers. Similarly, the sheet container 308 can have depressions of different depths, widths, and heights. To illustrate, the sheet container 308 can have a deep depression to form thick sheets of fish meat or a shallow depression for forming layers of fat or connective tissue layered between the thick sheets of fish muscle.

In addition to container-based formation, FIG. 3 further illustrates the method 304 of extrusion to form primary structures. As illustrated, the disclosed method may utilize extrusion to form a primary fiber. For example, the disclosed method comprises placing a cell mass 320 in an extruder 316 having a die 318. The extruder 316 contains a mechanism that propels the cell mass 320 through the die 318 to form the desired shape. To illustrate, the die 318 has cylindrical openings such that the cell mass 320 that is forced through the openings form a cylindrical primary fiber 324. In alternative examples, a die has a slotted opening, such that a cell mass that is forced through forms into a shape of a sheet.

While the die 318 illustrated in FIG. 3 has circular openings, the disclosed method may use dies having openings of different shapes. For example, the die 318 may have flat openings to form fettuccine-shaped strands of cell mass. In some implementations, the disclosed method utilizes a plurality of dies with various opening shapes. For example, each of the plurality of dies may have openings of a similar width but different heights, or vice versa. The use of dies having various opening shapes and sizes enables the disclosed method to form a cell mass into various structure types. When combined to form a cell-based-meat product, the various structure shapes form a complex stacked architecture.

The die 318 may have openings in various configurations. As illustrated in FIG. 3, the die 318 has openings organized in a circular array. In some implementations, the disclosed method utilizes a die having a linear array of openings such that the openings are aligned in one or more rows. More specifically, in some implementations, the openings are aligned in a single row such that no primary fiber is formed above or below any other fiber. The absence of overlapping fibers enables an even application of each primary fiber with the toughening agent.

As further illustrated in FIG. 3, the method 304 of extrusion can be used to form a primary sheet 326. For example, a cell mass 320 is extruded under a roller 322 to form the primary sheet 326. As mentioned previously, the cell mass 320 can comprise a combination of cells and a binder to facilitate the formation of intact sheets. The roller 322 flattens the cell mass 320 into one or more sheets. The sheets may be cut to a desired length to form the primary sheet 326.

Toughening agent is applied to the primary sheet 326 before, during, or after formation. To illustrate, in some embodiments, the cell mass 320 is sprayed with a toughening agent before being rolled. In some embodiments, the cell mass 320 is placed on a perforated belt so that toughening agent can be applied to the surface of the cell mass 320 that is in contact with the perforated belt. In another example, the roller 322 is coated with toughening agent, which transfers to the surface of the cell mass 320 during rolling. In yet another example, the toughening agent is applied to the primary sheet 326 after formation. For example, in some embodiments, the primary sheet 326 is pulled along a perforated conveyor belt and spray coated from above and/or below through the perforated belt. FIG. 4 and the accompanying discussion provide examples of applying the toughening agent to the formed primary structures.

In some embodiments, the roller 322 can be embossed to impart different textures to the primary sheet 326. For example, the roller 322 can have shallow impressions to form primary sheets having surface texture. In another example, the roller 322 has edges for cutting shapes in the cell mass. In such examples, the roller 322 punches holes of various shapes and sizes in the primary sheet 326.

Primary sheets with different surface textures and openings can be used in different ways to form cell-based-meat products. For example, the primary sheet 326 can be stacked with other primary sheets made of the same or different cell types to form distinct layers. Primary sheets with complimentary surface textures can be stacked to form complex interlocking layers of cell mass. Primary sheets may also be used to wrap other primary structures. For instance, primary sheets may be used to wrap primary fibers to mimic sheaths of connective tissue that hold together bundles of muscle fibers. In some implementations, primary sheets with holes are used to wrap bundles of primary fibers having toughened exterior surfaces to mimic epimysium, perimysium, or endomysium.

FIG. 3 illustrates the formation of the primary sheet 326. In some implementations, the primary sheet 326 is further processed to form primary structures of different shapes. For example, the primary sheet 326 can be sliced to form long and thin primary fibers.

As mentioned previously, the disclosed method comprises applying a toughening agent to exterior surfaces of the primary structures. FIG. 4 illustrates various methods for applying a toughening agent to primary structures in accordance with one or more embodiments. FIG. 4 illustrates methods 400 including a method 402 of spraying the primary structures, a method 404 of immersing the primary structures, and a method 406 of applying the toughening agent to containers.

FIG. 4 illustrates the method 402 of spraying the primary structures. Generally, the method 402 comprises applying the toughening agent by spraying the toughening agent on the exterior surfaces of the primary structures. As illustrated, a toughening agent 412a is sprayed using a nozzle 410. The toughening agent 412a coats the exterior surfaces of primary structures 408. In some implementations, the method 402 is used to apply to all surfaces of the primary structures 408. For example, the primary structures 408 can be placed on a slotted belt through which the toughening agent 412a is sprayed. In another example, the toughening agent 412a is applied first to one side of the primary structures 408. The primary structures 408 are flipped or turned, and the toughening agent 412a is applied to a second side of the primary structures 408.

FIG. 4 further illustrates the method 404 of immersing the primary structures. Generally, the method 404 comprises applying the toughening agent by immersing the primary structures in a bath comprising the toughening agent. As illustrated, the primary structures 408 are immersed in baths comprising the toughening agent 412b. In some examples, the disclosed method comprises placing freshly formed primary structures on a conveyor belt. The conveyor belt transports the primary structures 408 into one or more baths containing the toughening agent 412b. In another example, instead of using a conveyor belt, the method 404 comprises extruding the primary structures 408 directly into a bath of the toughening agent 412b. The primary structures 408 are collected out of the bath.

FIG. 4 also includes the method 406 of applying the toughening agent to containers. Generally, the method 406 comprises applying a toughening agent 412c to an interior surface of a container 414. For instance, the toughening agent 412c is sprayed into the depression of the container 414 to form a thin layer that will later act as a boundary for the primary structure. The disclosed method further comprises filling the container 414 with a cell mass 416. The disclosed method comprises applying the toughening agent 412c to the exposed surface of the cell mass 416. While FIG. 4 illustrates applying the method 406 to a container for forming a primary sheet, the method 406 may be utilized to apply the toughening agent 412c to a container for forming a primary fiber or another primary structure. In some embodiments, two or more of the different methods used to apply a toughening agent to a primary structure are combined, wherein a toughening agent is applied two or more times to a single primary structure.

FIG. 4 and the above paragraphs describe different methods used to apply a toughening agent to primary structures in accordance with one or more embodiments. The following paragraphs further detail different types and compositions of toughening agents that may be utilized in one or more embodiments. In one embodiment, a target texture is somewhere between an elastic gelatin and a crispy texture. In particular, the toughening agent results in the formation of textural variation akin to a shell-like structure (e.g., chocolate dipped ice cream) or a strong surface tension over a weaker interior (e.g., gelatin dessert), wherein the exterior surface at least momentarily arrests or slows the teeth during incision but then breaks or snaps away under the force of the advancing teeth. The purpose of the toughening agent is to create texture based on the directionality of meat fibers in a cell-based-meat product, wherein with each bite a person chewing the cell-based meat product of the present disclosure experiences a plurality of perceptible textural variations, whose organization and variable resistance to bite force together provide an indication of the teeth's relative orientation to the grain of the fibers and/or sheets. In some implementations, the toughening agent is formulated based on properties of the toughening agent. For instance, a formulation of a toughening agent may be more desirable if the resulting toughening agent is sticky and likely to adhere to primary structures. In some instances, a stickiness of a toughening agent is enhanced to facilitate a robust adherence between two or primary structures and/or other higher ordered structures.

Generally, toughening agents may comprise at least one of gelatin, gelatin substitutes, carb-based texturizers, food-based tougheners, collagen, fibroblasts, or lipids. Gelatin is a protein that, when activated, has an elastic texture. The concentration of gelatin within a toughening agent may be adjusted based on a desired texture. For example, gelatin may be bloomed or sprinkled into a liquid and set for a blooming period for optimal crystal hydration. Less gelatin may be used for softer textures. More gelatin may be used to create a firmer, but perhaps more rubbery, texture. Gelatin is activated by temperature. More specifically, gelatin sets when cooled.

As mentioned, a toughening agent may comprise gelatin substitutes. Gelatin substitutes may comprise agar-agar from red sea algae, carrageenan from seaweed, pectin (high or low methoxyl), vegan "j el" (including evaporated cane juice, vegetable gum, citric acid, potassium citrate, and beet powder), xantham gum, guar gum, arrowroot, kudzu, and others. Many of the listed gelatin substitutes are temperature activated, for instance, by heating or cooling.

Toughening agents may also comprise carb-based texturizers. Carb-based texturizers may include corn starch, amylose, transglutimase, starches, protein isolates, carbohydrates, sodium caseinate, teitolin, yeginate, texite, nitrates, nitrites, carrageenan, tertiary butylhydroquinone, phosphate additives, propyl gallate, pthallates, and others. Corn starch has properties that may be beneficial in a toughening agent. Generally, corn starch comprises two types of starch molecules (amylose and amylopectin) which can cross link with one another at high activation temperatures. In another example, amylose may be activated using vacuum drying. Activated amylose may offer gelation or crystallization. Some of these texturizers are activated using heat. Others are activated over time.

As mentioned, toughening agents comprise food-based tougheners. Food-based tougheners may comprise combinations of other components. For example, food-based tougheners include mixtures of carbohydrates and lipids. For example, food-based tougheners include breadcrumbs, ground/powdered rice, toasted rice cereals, and others.

In some implementations, a toughening agent comprises collagen. Collagen provides surface tension but also melts in the mouth upon consumption.

In some examples, a toughening agent comprises fibroblasts. Fibroblasts may require additional processing. For example, fibroblasts may be cultured under high shear stress to form fibrous tissue sheets. Using fibroblasts in a toughening agent beneficially provides a cell-based-meat product having fibroblasts as connective tissue between muscle fibers that creates a more realistic muscle morphology. In one example, fibroblasts are grown into shapes, strings, or thin sheets and incorporated into a toughening agent and organized such that their lengths run similar directions and are overlapping.

In some embodiments, toughening agents comprise lipids. Example lipids include plant-based oils such as olive oil, vegetable oil, etc. In another example, lipids include fatty cells like adipocytes.

In some implementations, different types of toughening agent are used to form a single cell-based-meat product. For example, a first type or formulation of toughening agent is used at a first level (e.g., primary structures), and a second type or formulation of toughening agent is used at a second level (e.g., secondary structures). In another example, different methods for application may correspond with particular toughening agent compositions. In some instances, it may be preferable to use a toughening agent that sets, cures, or activates without heat or under cooling to enable the formation of a raw, uncooked product.

The disclosed method further comprises arranging the primary structures comprising the toughened exterior surfaces to mimic structures in a target slaughtered meat. FIG. 5 illustrates example methods 500 of arranging primary structures to mimic structures in a target slaughtered meat in accordance with one or more embodiments. By way of overview, FIG. 5 illustrates a method 502 of utilizing a mold and a method 504 of weaving the primary structures.

FIG. 5 illustrates the method 502 of utilizing a mold. The method 502 comprises an act 506 of arranging primary structures into a mold and an act 508 of compressing the structures in the mold. As part of the act 506, the disclosed method comprises arranging primary structures having toughened exterior surfaces in a mold to mimic structures in a target slaughtered meat. As illustrated in FIG. 5, the disclosed method comprises arranging primary structures into molds of different shapes and sizes. More specifically, FIG. 5 illustrates a layering mold 518 and a chicken breast mold 512.

As shown in FIG. 5, the disclosed method comprises arranging primary structures (e.g., primary sheets) in the layering mold 518. In some implementations, primary structures are arranged in the layering mold 518 to mimic fish meat. As illustrated, the disclosed method comprises layering primary sheets of a first cell type 520 that resemble layers of meat. The primary sheets of the first cell type 520 may comprise sheets made of myoblasts. The disclosed method further comprises layering primary sheets of a second cell type 522 between the primary sheets of the first cell type 520. The primary sheets of the second cell type 522 may comprise adipocytes, fibroblasts, or a combination.

Figure 10:
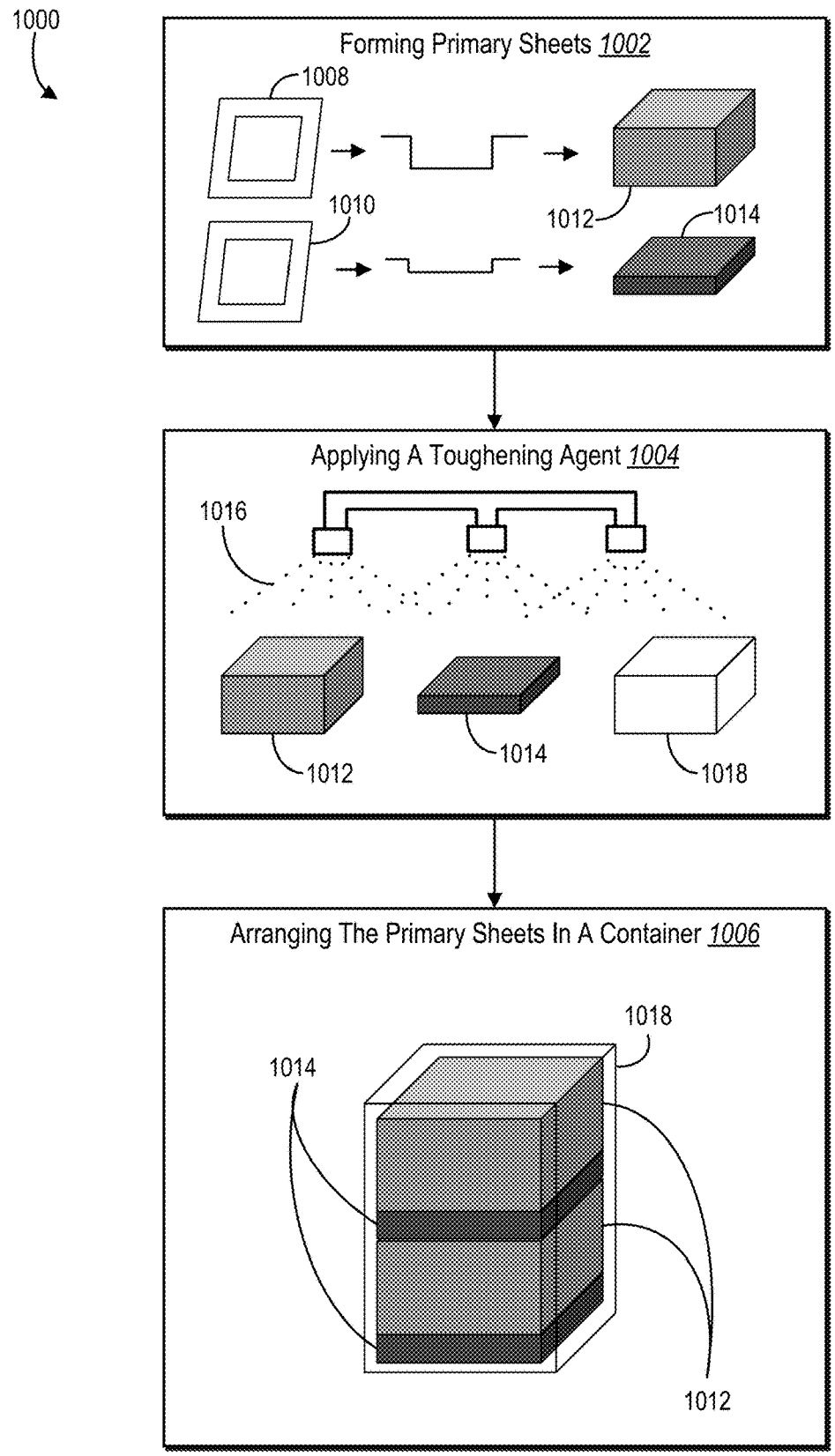

By layering the primary sheets of different cell types within the layering mold 518, the disclosed method forms full-size cuts of cell-based meat that resemble cuts of fish (e.g., tuna and salmon) in structure and architecture. FIG. 10 and the corresponding discussion further detail an example method for forming layered meat in accordance with one or more embodiments.

Figure 9:
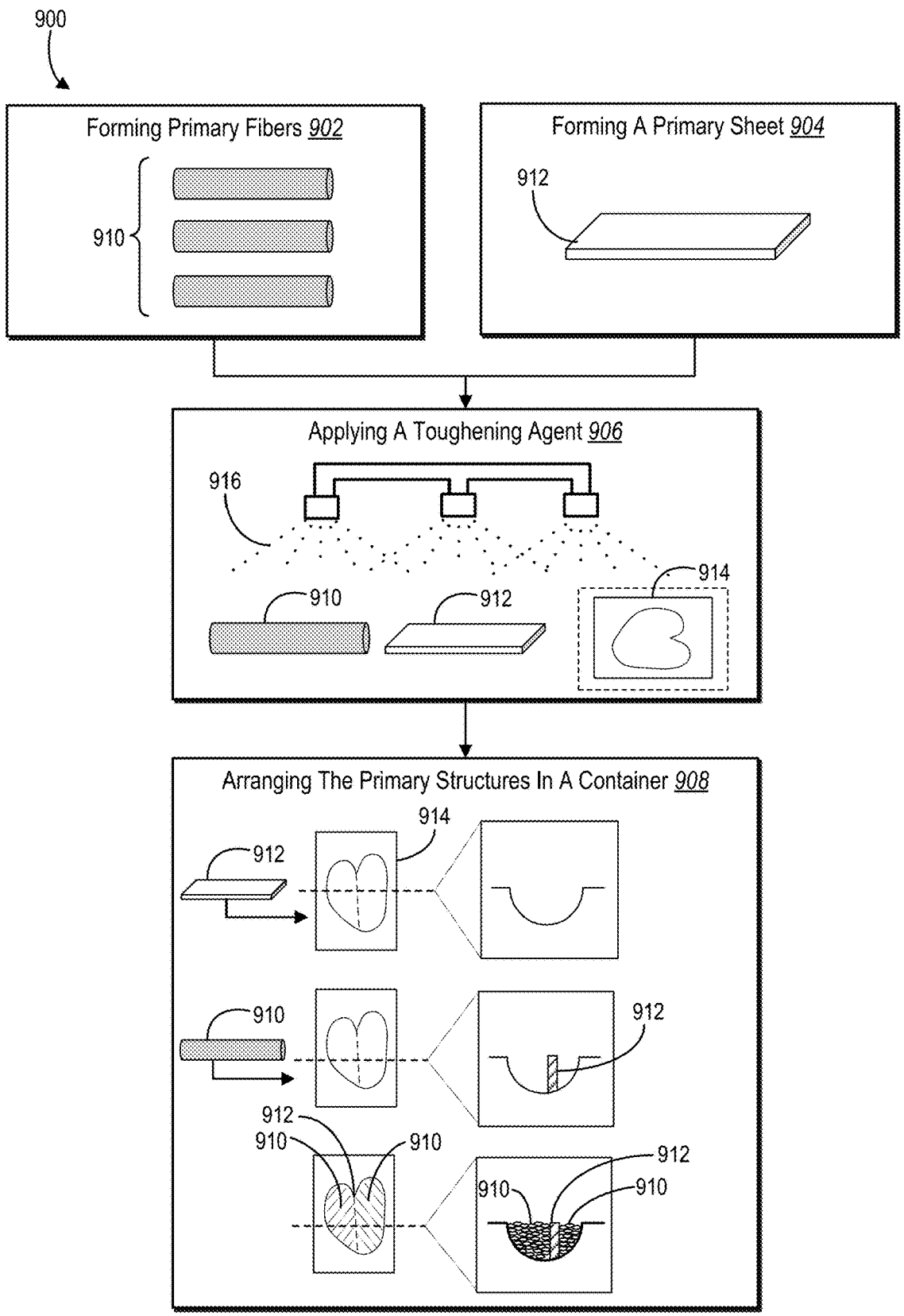

In some implementations, the act 506 may comprise arranging primary structures of different types into the same mold. For instance, the disclosed method may comprise arranging both primary sheets and primary fibers into the same mold. FIG. 5 further illustrates arranging primary structures into a chicken breast mold 512. Generally, the disclosed method comprises arranging a primary sheet perpendicular to an interior surface of the chicken breast mold 512, wherein the primary sheet mimics fascia connecting a tenderloin and a breast muscle. For example, the primary sheet may be placed perpendicularly along a divider 516. The disclosed method further comprises arranging primary fibers 514 perpendicular to the primary sheet. The primary fibers along a first side of the primary sheet form a tenderloin and the primary fibers along the second side of the primary sheet form the breast muscle. FIG. 9 and the corresponding discussion further detail forming a cell-based-meat product that mimics a chicken breast in accordance with one or more embodiments.

In some embodiments, the disclosed method comprises wrapping primary fibers in primary sheets before arranging them into a mold. For example, a plurality of primary fibers may be bundled together and then wrapped with a primary sheet to form a first-level fiber unit or a fiber bundle. The bundle of primary fibers may then be placed into a mold. In one example, a primary sheet is made of fat, collagen, both, or another combination of connective cells. In some embodiments, the primary sheet is stamped or otherwise texturized. The primary sheet is wrapped around one or more primary fibers comprising myocytes to make a first level fiber unit. Several fiber bundles may be grouped and further wrapped with primary sheets to form second-level fiber units. First-level, second-level, etc. fiber units may be arranged within molds of various shapes and sizes.

As further illustrated in FIG. 5, the disclosed method includes the act 508 of compressing the structures in the mold. Generally, when a mold is filled with primary structures, the disclosed method includes compressing the primary structures to form the cell-based-meat product. Compressing the primary structures within the mold removes air bubbles between the primary structures to strengthen bonds between primary structures. Furthermore, compressing the primary structures also forms the surface of the cell-based-meat product to the interior surface texture of the mold.

FIG. 5 illustrates two general methods for compressing the structures in the mold. In one example, the disclosed method utilizes a tamper 524 to mechanically press primary structures within a mold. The tamper 524 presses on an exposed primary structure within the mold. The applied pressure forces the primary structures deeper into the mold. In another example, the disclosed method utilizes a vacuum sealer to compress primary structures within a mold. For example, the chicken breast mold 512 is covered with a film and air is removed from the primary structures within the mold. FIG. 5 illustrates utilization of the tamper 524 to compress primary sheets within a layering mold and utilization of the vacuum sealer 534 for the chicken breast mold 512. The disclosed method may utilize the tamper 524 and/or the vacuum sealer 534 to compress primary structures of any type within any type and shape of mold.

As further illustrated in FIG. 5, the disclosed method may include the method 504 of weaving the primary structures. For instance, the method 504 comprises weaving primary structures to form a secondary structure. In one example, a cell mass is fed into extruders 532a, 532b, and 532c. The extruders form the cell mass into primary fibers 530a, 530b, and 530c. In some implementations, the primary fibers 530a-530c are fed through a guide ring and attached to a fiber braiding machine 525. The fiber braiding machine 525 comprises a rotating mechanism that twists the primary fibers 530a-530c and rotates the primary fibers 530a-530c to form a secondary fiber. As the primary fibers 530a-530c are fed out of the extruders 532a-532c, the fiber braiding machine 525 pulls away from the extruders 532a-532c. Cross-section 526 depicts a cross-section of a secondary fiber made by weaving together a plurality of primary fibers. As illustrated, the secondary fiber comprises twisted and interwoven primary fibers. The secondary fiber may be wound and stored on a spool 528. As explained below, FIG. 7 and the corresponding paragraphs further detail forming secondary fibers and tertiary fibers using a fiber braiding machine in accordance with one or more embodiments.

In some implementations, as part of the method 504 of weaving the primary structures, the extruders 532a-532c are moved to facilitate braiding or weaving of the primary fibers 530a-530c into secondary fibers. In such examples, the extruders 532a-532c are located at fixed positions relative to guide rings. The primary fibers 530a-530c are fed through individual guide rings and connected to the fiber braiding machine 525. As the extruders 532a-532c extrude the primary fibers 530a-530c, the extruders 532a-532c spin and rotate to intertwine the primary fibers 530a-530c. In such instances, the fiber braiding machine 525 comprises a mechanism that grasps the secondary fiber and pulls the secondary fiber toward the spool 528. In some implementations, instead of attaching the secondary fiber to the grasping mechanism, the disclosed method feeds the secondary fiber onto a series of wheels or rollers that compress the secondary fiber and reduce gaps between adjacent primary fibers. The series of wheels convey the secondary fiber to the spool 528, which winds and pulls the secondary fiber.

In some embodiments, prior to winding the secondary fibers around the spool 528, the disclosed method further compresses the secondary fibers. For instance, the disclosed method compresses primary fibers woven to form the secondary fiber to strengthen bonds between primary structures within the secondary fiber. In one implementation, the secondary fiber is fed onto a series of wheels 536. As illustrated by wheel cross-section 538, the wheels 536 have indented surfaces for accepting the secondary fiber. In some implementations, the wheels 536 are staggered such that the secondary fiber travels over one wheel and under a second wheel. The wheels 536 may also be placed to the left, right, or another face of the secondary fiber. The location of the wheels 536 relative to adjacent wheels and relative to the secondary fiber controls the amount of pressure applied to the secondary fiber.

As suggested by FIG. 5, in some implementations, the wheels 536 can move closer to or farther away from the secondary fiber. Closer wheels apply more pressure to the secondary fiber and exert a more powerful compression force than wheels located farther from the secondary fiber. In another example, adjacent wheels may be aligned with one another or have a height difference that causes a secondary fiber traversing the adjacent wheels to follow a tortuous path. A generally tortuous path may lead to the formation of a condensed and hardened secondary fiber. On the other hand, an arrangement of adjacent wheels that provides a generally linear path for a secondary fiber may lead to a formation of a malleable and soft fiber. The variable pressure applicable by the wheels 536 thereby allows for further control of fiber toughness, including modulation of a toughness of material interior to or coated by a toughening agent. In some embodiments, the movement of the wheels 536 serves to compact, to remove trapped air, and to form a tight secondary fiber. In some embodiments, the wheels 536 may have variable positions to enable formation of a secondary fiber with variable compression along its length. For example, a secondary fiber may have a compression gradient along its length; a secondary fiber may have one or more interspaced compressed regions; a secondary fiber may have compressed end regions and uncompressed middle regions; a secondary fiber may have uncompressed end regions and compressed middle regions; or some combination thereof. Compression approaches may vary according to the targeted conventional meat the secondary fibers are formed to imitate and any given combination of secondary fibers may use two or more compression approaches to provide variety for one or more groups of fibers and sheets. Similar compression methods can be applied to tertiary fibers, quaternary fibers, and the like. The compacted secondary fiber can be wound around the spool 528 for later processing.

In some implementations, and as will be described in additional detail below with respect to FIG. 7, the method 504 comprises weaving together primary structures of different types. For example, the disclosed method may weave together both primary fibers and primary sheets. For example, a primary sheet may be extruded from one of the extruders 532a-532c. The primary sheet may be stamped or otherwise texturized to provide textural variations within the secondary fiber. Like the primary fibers 530a-530c, the primary sheet is fed through a guide ring. The primary sheet guide ring may be larger or otherwise have a different shape to accommodate the primary sheet. The primary sheet is spun with the rotating mechanism with the primary fibers. In some instances, the primary sheet extruder is placed on the end of a rotatable extrusion line such that the primary sheet is regularly positioned on the exterior surface of the formed secondary fiber. In other words, the primary sheet forms a coating or covering around the secondary fiber, which is made of interwoven primary fibers. In this instance, the primary sheet mimics the connective tissue in animal muscle that hold muscle fibers together.

Furthermore, in some implementations, the disclosed method further comprises creating higher-order fibers by utilizing the secondary fibers. For example, a plurality of secondary fibers may be unspooled and fed through a guide ring into a rotating mechanism. In some implementations, the secondary fibers are interwoven with a primary sheet. The interwoven secondary fibers form a tertiary fiber that is then compressed and spooled. This process may be repeated to continue to form quaternary fibers, quinary fibers, senary fibers, etc. The complex structure formed by interweaving fibers results in a multilayered fiber mimicking the structure of muscle, which may then be organized to mimic a target cut of conventional meat.

Figure 6:
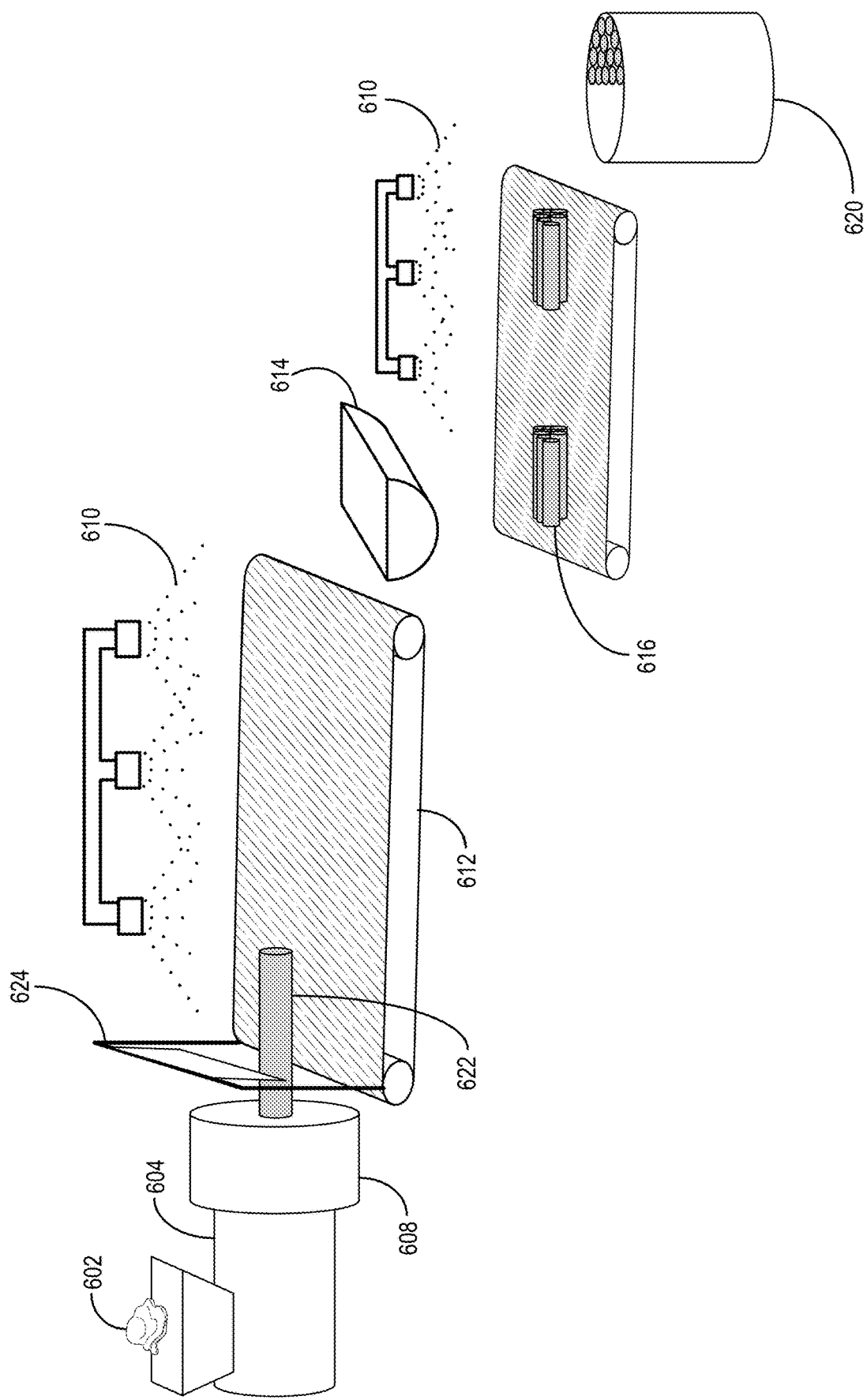
FIG. 6 illustrates an example workflow for forming and arranging primary structures using a mold in accordance with one or more embodiments of the present disclosure.

FIGS. 1-5, the corresponding text, and the examples provide several different methods for forming cell-based-meat products using primary structures in accordance with one or more embodiments. The methods described above may be utilized in various workflows that may be scaled for use in production. FIGS. 6-7 illustrate example workflows for forming cell-based-meat products in accordance with one or more embodiments. FIG. 6 illustrates an example workflow for arranging primary fibers within one or more molds in accordance with one or more embodiments. FIG. 7 illustrates an example workflow for weaving primary fibers and a primary sheet to form higher-order fibers in accordance with one or more embodiments.

As mentioned, FIG. 6 illustrates an example workflow for forming a cell-based-meat product by arranging primary structures in a mold. As illustrated, a cell mass 602 is placed into an extruder 604. The extruder 604 forces the cell mass 602 through a die 608. Through this process, the cell mass is formed into a primary fiber 622. The primary fiber 622 travels along a conveyor belt 612. The primary fiber 622 may be cut to a desired length using a blade 624. In some implementations, the desired length is determined based on a length of a mold 614. For example, the primary fiber 622 is cut to fit the length of the mold 614. In some implementations, toughening agent 610 is applied to the primary fiber 622 as the primary fiber 622 travels via the conveyor belt 612.

The primary fiber 622 travels over the length of the conveyor belt 612 and falls into the mold 614. Once the mold 614 is filled, the mold 614 is moved and another empty mold fills its place. The filled mold 614 can be vacuum sealed or mechanically pressed, as described above, to facilitate forming. In some implementations, the mold 614 has the shape of a final cell-based-meat product. For example, the mold 614 can form long cylindrical cell-based-meat products that, when cut across the "grain," resemble cuts of steak or crab meat.

In some implementations, the filled mold forms a secondary structure 616 that can be combined to form higher-ordered cell-based meat products. To illustrate, the mold 614 is emptied, and the secondary structure 616 is placed on a second conveyor belt. The toughening agent 610 is applied to the secondary structure 616. In some implementations, the toughening agent 610 applied to the secondary structure 616 is different than the toughening agent applied to the primary fiber 622. For example, different toughening agents are used to accomplish different textures at different structural levels. By contrast, in some implementations, the toughening agent 610 is applied to both the primary fiber 622 and the secondary structure 616.

As further shown in FIG. 6, the secondary structure 616 travels the length of the second conveyor belt and is dropped into a secondary mold 620. Once the secondary mold 620 is filled, the secondary mold 620 is removed and an empty secondary mold put in its place. The secondary mold can be vacuum sealed or mechanically pressed to form a tertiary structure.

The disclosed method may comprise repeating the above-described steps using progressively larger molds to form increasingly complex structures of fibers. More specifically, this process may continue until fibers or shapes of a desired size are formed (e.g., 5-10 times). In some implementations, the described methods are repeated until a secondary, tertiary, quaternary, or other higher-level structure is placed in a final mold, which has the shape of a cell-based-meat product. For example, the final mold can resemble a chicken breast, salmon filet, beef steak, or any cut of meat.

Figure 7:
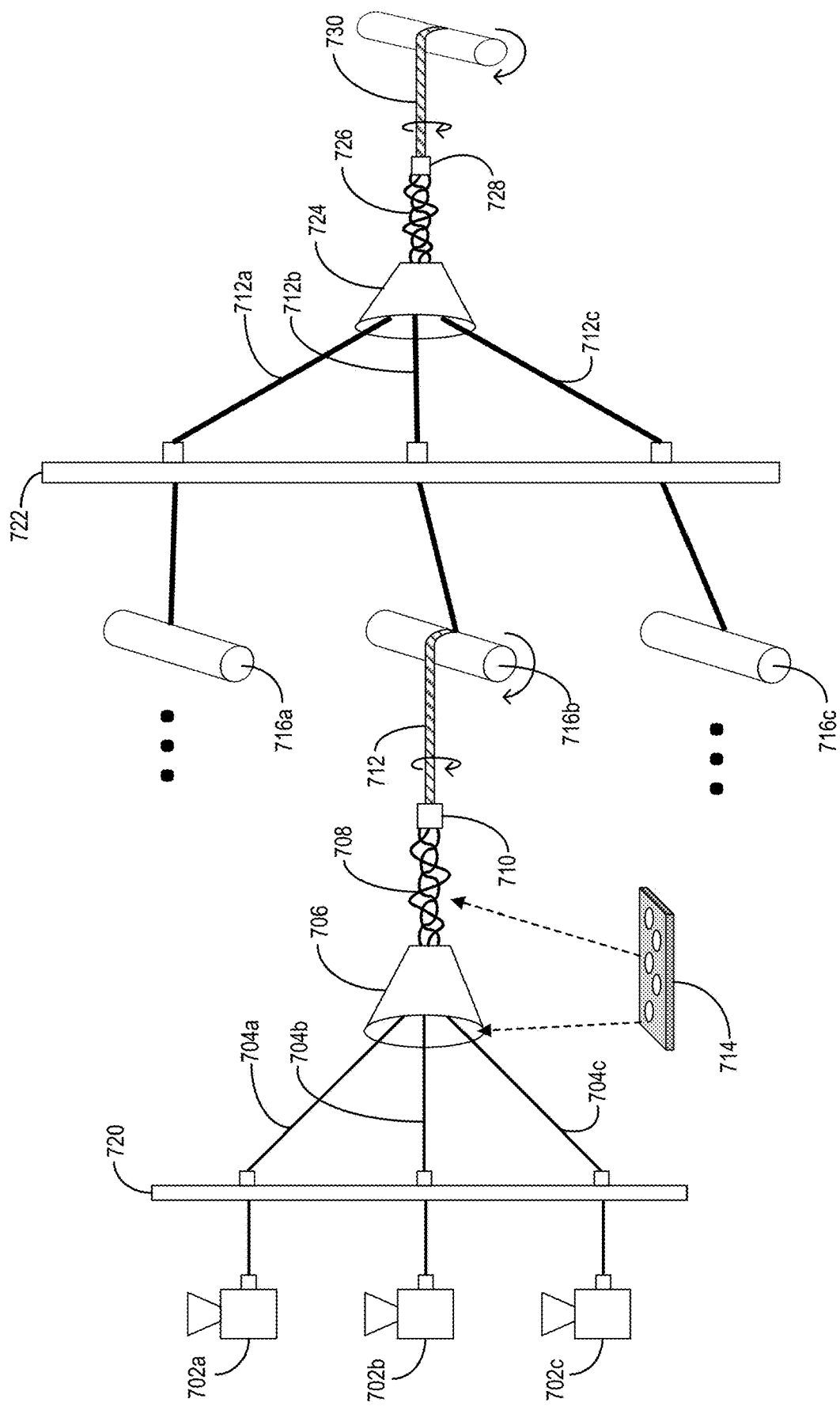
FIG. 7 illustrates an example workflow for forming and weaving primary structures in accordance with one or more embodiments of the present disclosure.

FIG. 7 and the corresponding paragraphs describe an example workflow for forming higher-order fibers by weaving lower-order fibers. As illustrated in FIG. 7, cell mass is fed into extruders 702a, 702b, and 702c. The cell mass is extruded into primary fibers 704a, 704b, and 704c. The primary fibers 704a-704c can be fed through a guide ring 706 and attached to a fiber braiding machine 710. The fiber braiding machine 710 causes the primary fibers 704a-704c to form woven fibers 708. In some implementations, the woven fibers 708 are compressed (e.g., by wheels) to form a secondary fiber 712b, which is wound onto a spool 716b.

As mentioned previously, in some implementations, the extruders 702a-702c rotate to interweave the primary fibers 704a-704c. For example, the fiber braiding machine 710 is replaced with a grasping mechanism, and each of the primary fibers 704a-704c is threaded through an eyelet in a rotating mechanism 720. The rotating mechanism 720 manipulates the primary fibers 704a-704c and the extruders 702a-702c to form the woven fibers 708. Again, the woven fibers 708 may be compressed and wound around the spools 716a-716c.

In some implementations, the disclosed method comprises integrating a primary sheet 714 into the woven fibers 708. For example, a secondary extruder may be used to form the primary sheet 714. In some instances, the primary sheet 714 is stamped with sporadically placed holes to provide variations. The primary sheet 714 may be otherwise texturized. As illustrated, in some implementations, the primary sheet 714 is fed through the guide ring 706 and attached to the fiber braiding machine 710. The primary sheet 714 may be positioned externally relative to the primary fibers 704a-704c such that the primary sheet 714 forms a layer around the woven fibers 708. For instance, the sheet extruder that forms the primary sheet 714 is positioned on an end of a rotatable extrusion line such that the primary sheet 714 is regularly positioned on an exterior surface of the formed secondary fiber. The primary sheet 714 may be compressed together with the woven fibers 708 to form the secondary fibers 712a-712c. In some embodiments, instead of being fed through the guide ring 706 with the primary fibers 704a-704c, the primary sheet 714 is simply wrapped around the woven fibers 708.

As further illustrated in FIG. 7, secondary fibers 712*a*-712*c* may be unspooled from the spools 716*a*-716*c*, respectively, and fed through a second guide ring 724 into a second fiber braiding machine 728 to form a tertiary woven fiber 726. In some implementations, a sheet extruder also forms the primary sheet 714 for integration into the tertiary woven fiber 726. The tertiary woven fiber 726 is further compressed by a series of wheels to form a tertiary fiber 730, which may be wound on a spool. As with the formation of the secondary fibers 712*a*-712*c*, formation of the tertiary fiber 730 may utilize a rotating mechanism 722. The process described above may be continued to form quaternary fibers, quinary fibers, etc. by repeating the process as many as 5-10 times, for instance. In some instances, lower ordered fibers are not spooled but instead fed immediately into further braiding machines, with optional wheel driven compression between braiding steps, wherein a plurality of primary fibers are continuously formed into a higher ordered braided fiber. The resulting cell-based-meat product comprises a multi-layered fiber with a structure similar to the structure of a target slaughtered meat.

As suggested above, the toughening agent may be applied at various places within the workflow illustrated in FIG. 7. In some examples, the rotating mechanism 720 and the rotating mechanism 722 have applicators at the eyelets through which the primary fibers 704*a*-704*c* and the secondary fibers 712*a*-712*c* are threaded. As the primary fibers 704*a*-704*c* and the secondary fibers 712*a*-712*c* are drawn through the rotating mechanism 720 and the rotating mechanism 722, they are coated (or come into contact) with one or more toughening agents. In another example, a spray applicator is attached to the guide ring 706 or the second guide ring 724. In this example, the toughening agent is sprayed onto the primary fibers 704*a*-704*c*, the secondary fibers 712*a*-712*c*, and/or the primary sheet 714 as they begin to interweave. In some implementations, toughening agent is applied by immersion. More specifically, the extruders 702*a*-702*c* may extrude the primary fibers 704*a*-704*c* into a toughening agent bath where the primary fibers 704*a*-704*c* are interwoven. Similarly, the secondary fibers 712*a*-712*c* may be unspooled in a different or the same toughening agent bath.

Figure 8:
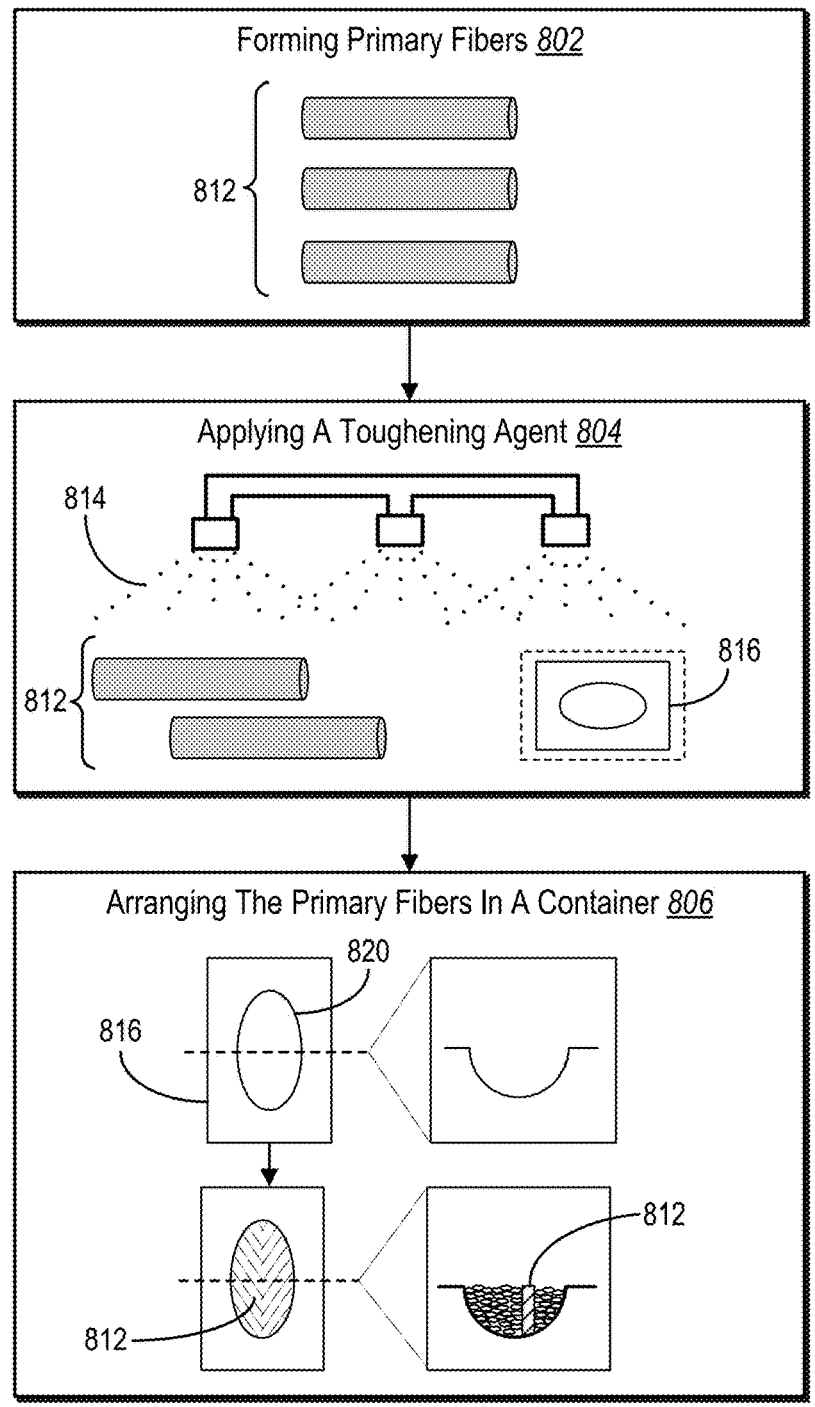
FIGS. 8-10 illustrate example methods for forming various target slaughtered meats including crab meat, poultry breast, and fish meat in accordance with one or more embodiments of the present disclosure.

The methods, techniques, components, and/or devices used to form a cell-based meat product may be used to form cell-based-meats resembling several types of slaughtered meats. FIGS. 8-10 illustrate an example series of acts for forming specific types of cell-based meat. More specifically, FIG. 8 illustrates forming cell-based-meat that mimics shellfish (e.g., a crab claw) in accordance with one or more embodiments. FIG. 9 illustrates forming cell-based-meat that mimics a poultry breast in accordance with one or more embodiments. FIG. 10 illustrates forming layers of primary structures to mimic the structure and form of fish meat in accordance with one or more embodiments.

As mentioned, FIG. 8 illustrates the formation of a cell-based-meat product that mimics shellfish. More specifically, FIG. 8 illustrates the formation of a crab claw. By way of overview, FIG. 8 illustrates a series of acts 800 comprising an act 802 of forming primary fibers, an act 804 of applying a toughening agent, and an act 806 of arranging the primary fibers in a container.

The series of acts 800 includes the act 802 of forming primary fibers. Generally, the disclosed method forms primary fibers 812 using methods described above in the discussion accompanying FIG. 3. The primary fibers are formed using a cell mass grown comprising shellfish cells. For example, in some implementations, the primary fibers 812 comprise crab animal cells. More specifically, in some embodiments, the primary fibers 812 are formed using a container having depressions that mimic the size of a typical fiber of crab meat. For example, the container may have depressions 2 in. in length, ⅛ in. in width, and ⅛ in. in depth. The container may be formed by pressing an object with the desired dimensions at regular intervals into a polycarbonate sheet. The act 802 comprises coating depressions of the container with a toughening agent and filling the depressions with the cell mass of choice. For instance, the disclosed method comprises filling the depressions with crab stem cells, myoblasts, fibroblasts, etc. The cell mass may be pressed into the depressions and excess removed by dragging an applicator across the surface of the container. The exposed portion of the cell mass is further spray coated with toughening agent and allowed to set. In some implementations, proto-fibers in the container are aligned using methods described above in the discussion accompanying FIG. 2.

As further shown in FIG. 8, in some implementations, the disclosed method comprises processing the primary fibers 812. For example, the cell mass may be vacuum sealed in the container to remove air bubbles and cause the cell mass to take on the shape of the container. Additionally, the disclosed method may induce solidification of the toughening agent so that the primary fibers 812 hold their form. For example, the disclosed method may flash heat, flash freeze, induce chemical bonding, or otherwise activate the toughening agent. In some implementations, methods for inducing solidification of the toughening agent are utilized before placing the cell mass in the container. In any case, the primary fibers 812 are collected, for example, by removing them from the containers. In some implementations, the primary fibers 812 are organized and arranged to be parallel.

FIG. 8 further includes the act 804 of applying a toughening agent. For example, the disclosed method comprises applying a toughening agent 814 to the exterior surfaces of the primary fibers 812. In some examples, the toughening agent 814 has already been applied during the formation of the primary fibers 812. In some implementations, the disclosed method comprises applying the toughening agent to an interior surface of a mold 816.

In addition to forming primary fibers and applying a toughening agent, in some cases, the series of acts 800 further comprises an additional act of forming the mold 816. In one example, a depression 820 in the mold 816 is formed by introducing one or more depressions into a tray. For example, an item the size of a crab claw can be pressed into a tray. As illustrated, the item is shaped roughly like an American football. The depression in the mold 816 can roughly have the dimensions of 2⅛" long, 1½" wide, and 1" deep, or otherwise match the size of a crab claw.

Furthermore, in some embodiments, the series of acts 800 further comprises an optional act of bundling the primary fibers 812 to form fiber bundles. For example, the primary fibers 812 may be woven to form secondary fibers. In another example, the primary fibers 812 are bundled by wrapping primary sheets around a plurality of primary fibers.

As further shown in FIG. 8, the series of acts 800 comprises the act 806 of arranging the primary fibers (and/or fiber bundles) in a container. Generally, the act 806 comprises filling the depression of the mold 816 with the primary fibers 812. In some implementations, the fibers all traverse the same general direction. If primary fibers placed in the mold 816 are longer than the mold 816, the disclosed method may comprise using a stamp press to cut the fibers and remove excess. The primary fibers 812 or fiber bundles may be compressed into the depression for space filling purposes. The exposed surfaces of the primary fibers 812 may be spray coated with toughening agent. The combined primary fibers and/or the fiber bundles take on a higher structure of a full cut of meat.

The disclosed method forms a formed cell-based meat by compressing the primary fibers and/or the bundle fibers in the mold 816. In some embodiments, the series of acts 800 includes additional acts for processing the formed cell-based meat. In one example, the primary fibers are vacuum sealed in the mold 816 to remove air bubbles and cause the primary fibers and/or the fiber bundles to take on the shape and form of the mold 816.

Although not depicted in FIG. 8, in some cases, additional acts of processing the formed cell-based meat comprises inducing solidification of the applied toughening agent. For instance, the disclosed method may comprise flash heating, flash freezing, chemical bonding, etc. the formed cell-based meat such that heat transfer to and from the cell-based meat is limited. The formed cell-based meat can be removed from the mold 816 and prepared for consumption. In other examples, the formed cell-based meat is packaged while still within the mold 816 and prepared for consumption. The formed cell-based meat illustrated in FIG. 8 mimics the structure of a crab claw.

FIG. 9 illustrates a series of acts for forming a cell-based-meat product that mimics the structure of a poultry breast. For example, the cell-based-meat product can mimic a chicken breast or a turkey breast. By way of overview, the series of acts 900 comprises an act 902 of forming primary fibers, an act 904 of forming a primary sheet, an act 906 of applying a toughening agent, and an act 908 of arranging the primary structures in a container.

As illustrated in FIG. 9, the series of acts 900 includes an act 902 of forming primary fibers. The primary fibers may be formed using any of the methods described above in the discussion accompanying FIG. 3. In some embodiments, the disclosed method comprises forming primary fibers 910 by using a fiber container. The fiber container has elongated depressions having a preferred fiber size and shape.

As above, a toughening agent can be applied. For instance, the fiber container may be spray coated with a toughening agent or texturizer. In some implementations, the toughening agent is activated before adding a cell mass to the container. A cell mass is added to the coated tray, and a toughening agent is optionally sprayed on top of the exposed cell mass. In some implementations, the toughening agent applied to the cell mass is activated. The fiber container with the cell mass may be covered with a polymer and vacuum sealed. The formed primary fibers 910 are removed from the fiber container.

In some implementations, the primary fibers 910 are further combined or bundled to form secondary or higher-order fibers. For example, the primary fibers 910 may be combined to form fiber bundles. Fiber bundles may comprise interwoven primary fibers, primary fibers wrapped and held together using a primary sheet, or another means.

As further shown in FIG. 9, the series of acts 900 to form fibers mimicking a poultry breast further includes the act 904 of forming a primary sheet. Generally, the primary sheet mimics fascia that connects a tenderloin and a breast muscle in a poultry breast. The primary sheet may be formed using any of the methods described above in the discussion accompanying FIG. 3. More specifically, in some implementations, the primary sheet 912 is formed using a sheet container. In some cases, the sheet container has a rectangular depression. The sheet container may be spray coated with toughening agent or texturizer. The toughening agent or texturizer may be activated. For example, the toughening agent is activated by cooling or heating the sheet container.

A cell mass is added to the sheet container. More specifically, the cell mass comprises adipocytes, fibroblasts, or both. The cell mass is forced into the depression of the sheet container, and toughening agent may be applied to the exposed surface of the cell mass. In some examples, the toughening agent applied to the cell mass is activated. Furthermore, in some embodiments, the cell mass is vacuum sealed within the sheet container. For example, the filled container depression is covered with a polymer and vacuum sealed. The primary sheet 912 is removed from the sheet container.

In addition to adding a cell mass to a container, the series of acts 900 to form fibers mimicking a poultry breast includes the act 906 of applying a toughening agent. The disclosed method may include spray coating a toughening agent 916 onto the primary fibers 910, the primary sheet 912, and/or a mold 914. The mold 914 comprises a tray having a depression in the shape of the desired breast meat (e.g., chicken breast). In some implementations, the toughening agent is activated prior to arranging the primary fibers 910 and/or the primary sheet 912 in the mold 914.

The series of acts 900 to form fibers mimicking a poultry breast includes the act 908 of arranging the primary structures in a container. In some embodiments the primary sheet 912 is first placed into the mold 914. More specifically, the primary sheet 912 is placed along the length of the breast-shaped depression (e.g., along the dotted line illustrated in FIG. 9). The disclosed method further comprises placing the primary fibers 910 (and/or fiber bundles) on either side of the primary sheet 912. For example, a first set of primary fibers or fiber bundles placed on one side of the primary sheet 912 mimic the shape of a tenderloin in a poultry breast. A second set of primary fibers or fiber bundles placed on the other side of the primary sheet 912 mimic a shape of the breast muscle.

In some implementations, the disclosed method comprises additional acts of vacuum sealing the primary sheet 912 and the primary fibers 910 within the mold 914. In another additional act, a second primary sheet is added on top of the formed cell-based meat to mimic skin (e.g., chicken skin, turkey skin, etc.).

As mentioned, FIG. 10 illustrates the formation of a cell-based-meat product that mimics a cut of fish meat in accordance with one or more embodiments. By way of overview, FIG. 10 illustrates a series of acts 1000 including an act 1002 of forming primary sheets, an act 1004 of applying a toughening agent, and an act 1006 of arranging the primary sheets in a container.

The act 1002 comprises forming primary sheets. Generally, the act 1002 forms primary sheets using any method described above in the paragraphs corresponding to FIG. 3. More specifically, in some examples, primary sheets are formed using a first container 1008 and a second container 1010. The first container 1008 and the second container 1010 have square or rectangular depressions. In some examples, the first container 1008 has a deeper depression for forming sheets corresponding with sheets of meat while the second container 1010 has a shallower depression for forming sheets corresponding with sheets of connective tissue or fat.

The disclosed method may comprise applying a toughening agent to the inside surfaces of the first container 1008 and the second container 1010. The toughening agent may be activated prior to placing a cell mass within the first container 1008 and/or the second container 1010.

Furthermore, in some embodiments, the first container 1008 and/or the second container 1010 can be spray coated with lipids. More specifically, some fish (like tuna) is less fatty than other fish (like salmon). Thus, instead of forming primary sheets of fatty tissue, the disclosed method may comprise spray coating the first container 1008 with lipids and omitting use of the second container 1010. In such examples, the cell-based-meat product will be made of layers of cells coated in lipid.

As part of the act 1002, the primary sheets are formed by forcing cells of different types into the containers. The disclosed method comprises forming primary sheets made of cells. For example, a cell mass of a first type may be forced into the first container 1008. The first type may comprise myocytes or myoblasts. The disclosed method further comprises forming primary sheets made of fat or other connective tissue. More specifically, a cell mass comprising adipocytes is forced into a second container 1010. The depression of the second container 1010 has less depth to form a thinner sheet relative to the first container 1008. In either case, the disclosed method may comprise applying a toughening agent to the exposed surface of the cell mass. Additionally, in some implementations, the cell mass is sealed within the respective container using vacuum sealing. The disclosed method further comprises removing a primary sheet 1012 from the first container 1008 and a primary connective sheet 1014 from the second container 1010.

In some embodiments, the disclosed method further comprises the act 1004 of applying a toughening agent. Generally, a toughening agent 1016 is applied to exterior surfaces of the primary sheet 1012 and the primary connective sheet 1014. Furthermore, the disclosed method comprises applying the toughening agent 1016 to an interior surface of the mold 1018.

As further illustrated in FIG. 10, the disclosed method comprises the act 1006 of arranging the primary sheets in a container. The act 1006 comprises layering primary sheets in the mold 1018 such that layers alternate between myocytes and connective tissue. For example, and as illustrated in FIG. 10, the primary sheets are layered such that the primary connective sheet 1014 is layered between the primary sheets 1012. In some implementations, cutting the stack along its height and perpendicular to the grain forms slabs of fish (e.g., salmon, tuna, etc.) meat. Additionally, or alternatively, the primary sheets may be arranged in a curved or round configuration. For example, some cuts of fish include more rounded architecture. Variations in structure can be accomplished using containers with different depression shapes, or molds with different shapes.

FIGS. 8-10 illustrate example methods for forming cell-based-meat products that mimic structures in specific types of target slaughtered meat (e.g., poultry breast, shellfish, and fish). The disclosed methods may be used to form additional types of target slaughtered meats. For instance, the disclosed method may be used to form a cell-based-meat ham. Generally, the cell-based-meat ham may include fibers or sheets that spiral out from a common origin point. In another example, a cell-based-meat steak can be formed by combining numerous parallel sheets and fibers where a percentage of fibers comprise adipocytes or other cells with high fat concentrations to provide appropriate marbling.

Figure 11:
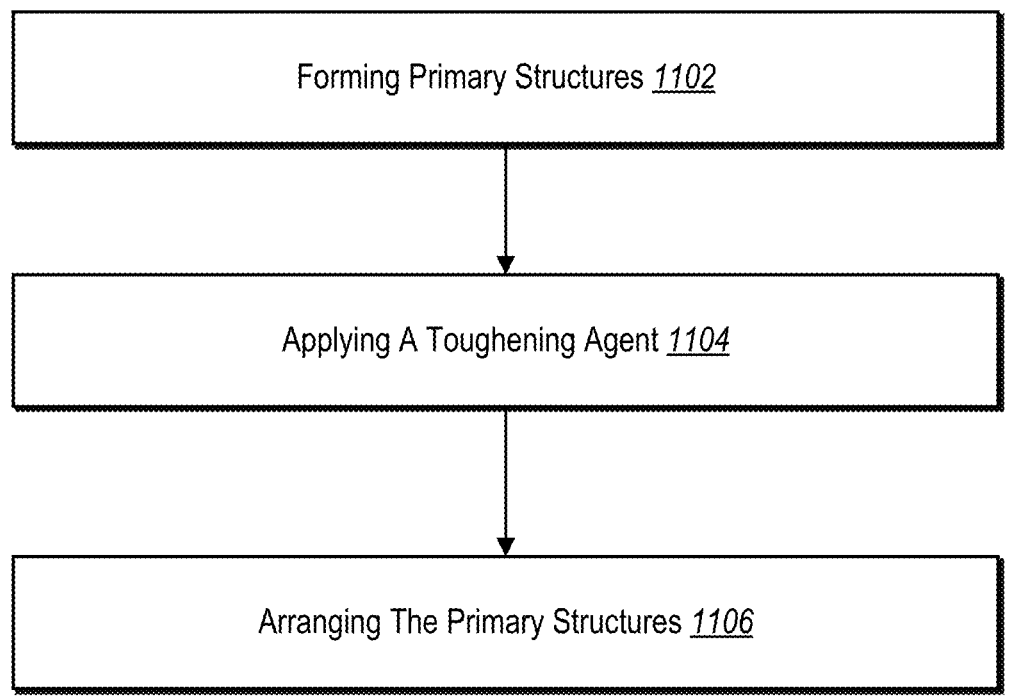
FIGS. 11-13 illustrate series of acts for arranging primary structures in accordance with one or more embodiments of the present disclosure.
Figure 12:
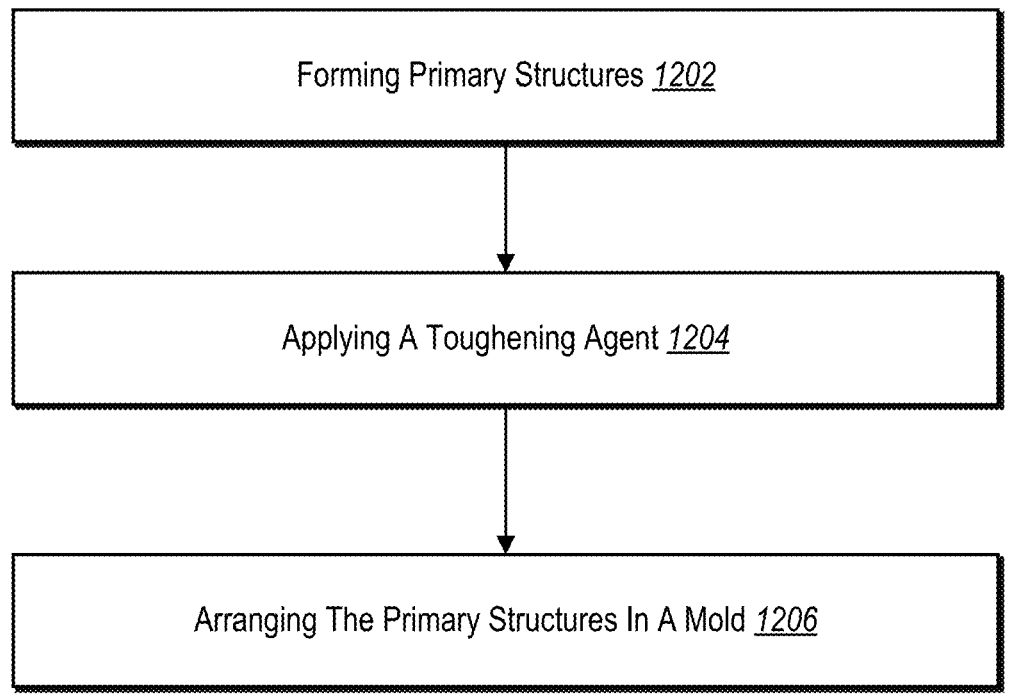
Figure 13:
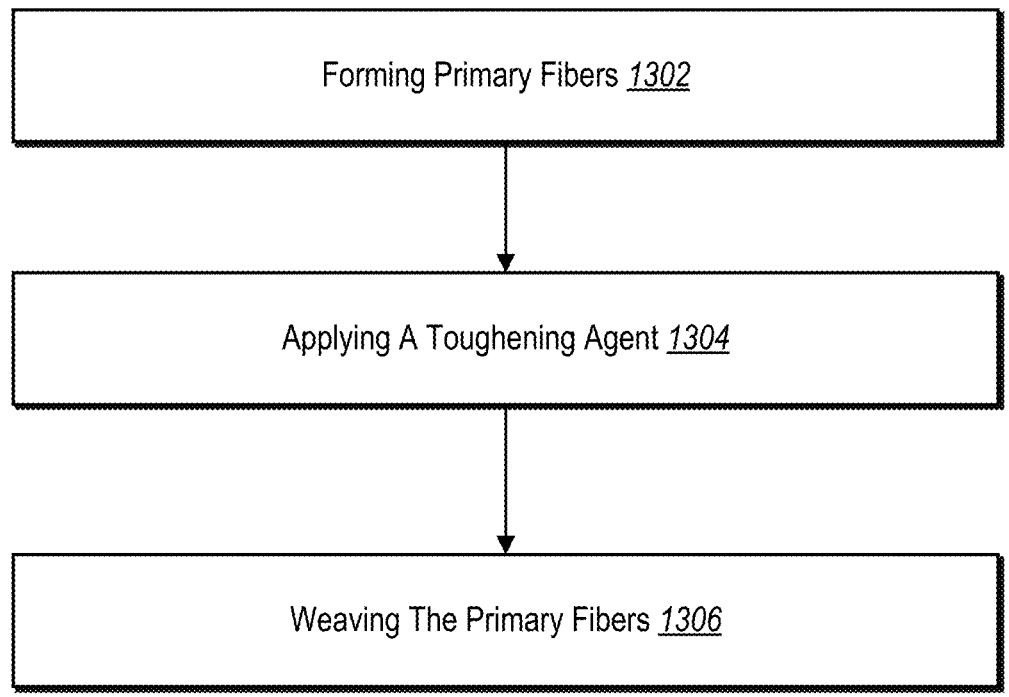

FIGS. 1-10, the corresponding text, and the examples provide several different systems, methods, techniques, components, and/or devices relating to forming a cell-based-meat product in accordance with one or more embodiments. In addition to the above description, one or more embodiments can also be described in terms of flowcharts including acts for accomplishing a particular result. FIGS. 11-13 illustrate such flowcharts of acts. The acts described herein may be repeated or performed in parallel with one another or in parallel with different instances of the same or similar acts.

By way of overview, FIG. 11 illustrates a series of acts 1100 comprising an act 1102 of forming primary structures, an act 1104 of applying a toughening agent, and an act 1106 of arranging the primary structures. In some implementations, the primary structures comprise at least one primary fiber and at least one primary sheet. Furthermore, in some embodiments, arranging the primary structures comprises positioning the at least one primary fiber at an angle relative to the at least one primary sheet. More specifically, in some implementations, the angle is between 10 degrees and 80 degrees. Furthermore, in some implementations, the primary structures are arranged to mimic a muscular architecture of a target cut of meat.

The series of acts 1100 includes the act 1102 of forming primary structures. In particular, the act 1102 comprises forming a cell mass into primary structures. In some embodiments, the cell mass comprises cells of a type from at least one of myocytes, adipocytes, or fibroblasts. In some implementations, the primary structures comprise at least one of primary fibers or primary sheets. In one or more embodiments, the act 1102 further comprises forming the cell mass into the primary structures by forcing the cell mass through an extruder. In some embodiments, the act 1102 comprises forming the cell mass into the primary structures by filling, with the cell mass, containers having shapes of the primary structures.

FIG. 11 further illustrates the act 1104 of applying a toughening agent. In particular, the act 1104 comprises applying a toughening agent to at least a portion of an exterior surface of the primary structures. In some examples, the act 1104 comprises applying the toughening agent by: applying the toughening agent to an interior surface of the containers; filling the containers with the cell mass; and applying the toughening agent to an exposed surface of the cell mass. In some implementations, the act 1104 further comprises applying the toughening agent by spraying the toughening agent on the exterior surfaces of the primary structures. Furthermore, in some examples, the act 1104 comprises applying the toughening agent by immersing the primary structures in a bath comprising the toughening agent. In some implementations, the toughening agent comprises at least one of gelatin, gelatin substitutes, carb-based texturizers, food-based tougheners, collagen, or fibroblasts.

The series of acts 1100 illustrated in FIG. 11 further comprises the act 1106 of arranging the primary structures. In particular, the act 1106 comprises arranging the primary structures comprising at least partially toughened exterior surfaces to mimic structures in a target slaughtered meat. In some embodiments, arranging the primary structures further comprises positioning a plurality of fibers such that at least a portion of lengths of the plurality of fibers are parallel. In some implementations, the series of acts 1100 further comprises an additional act of organizing proto-fibers in the cell mass prior to or during forming the cell mass into primary structures.

Additionally, in some embodiments, the series of acts 1100 further or alternatively comprises an act of arranging the primary structures comprising the at least partially toughened exterior surfaces within a mold having a shape of a cut of comestible meat. In some implementations, the series of acts 1100 further or alternatively comprises an act of vacuum sealing the mold and the arranged primary structures to form the cell-based-meat product. Furthermore, in some embodiments, the series of acts 1100 further or alternatively comprises an act of compressing the arranged primary structures within the mold to form the cell-based-meat product. In some embodiments, the series of acts 1100 further or alternatively comprises an act of applying the toughening agent to an interior surface of the mold.

By way of overview, FIG. 12 illustrates a series of acts 1200 comprising an act 1202 of forming primary structures, an act 1204 of applying a toughening agent, and an act 1206 of arranging the primary structures in a mold.

The series of acts 1200 comprises the act 1202 of forming primary structures. In particular, the act 1202 comprises forming a cell mass into primary structures. In some implementations, the primary structures comprise at least one of primary fibers or primary sheets.

As illustrated in FIG. 12, the series of acts 1200 further includes the act 1204 of applying a toughening agent. In particular, the act 1204 comprises applying a toughening agent to exterior surfaces of the primary structures.

FIG. 12 further illustrates the act 1206 of arranging the primary structures in a mold. In particular, the act 1206 comprises arranging the primary structures comprising the toughened exterior surface in a mold to mimic structures in a target slaughtered meat. In some embodiments, arranging the primary structures to mimic structures in the target slaughtered meat comprises: arranging a primary sheet perpendicular to an interior surface of a mold, wherein the primary sheet mimics fascia connecting a tenderloin and a breast muscle; and arranging primary fibers perpendicular to the primary sheet on each side of the primary sheet, wherein: a first set of primary fibers on a first side of the primary sheet mimic a shape of the tenderloin; and a second set of primary fibers on a second side of the primary sheet mimic a shape of the breast muscle. Furthermore, in some implementations, arranging the primary structures to mimic structures in the target slaughtered meat comprises: arranging, in a mold, primary sheets of a first cell type mimicking layers of meat; and layering, between the primary sheets of the first cell type, primary sheets of a second cell type mimicking layers of fat.

In some embodiments, the series of acts 1200 further includes an act of vacuum sealing the mold and the arranged primary structures to form the cell-based-meat product. Additionally, or alternatively, the series of acts 1200 includes an additional act of compressing the arranged primary structures within the mold to form the cell-based-meat product. Furthermore, in some implementations, the series of acts 1200 includes an additional act of applying the toughening agent to an interior surface of the mold.

By way of overview, FIG. 13 illustrates a series of acts 1300 comprising an act 1302 of forming primary fibers, an act 1304 of applying a toughening agent, and an act 1306 of weaving the primary fibers.

FIG. 13 illustrates the act 1302 of forming primary fibers. In particular, the act 1302 comprises forming a cell mass into primary fibers.

The series of acts 1300 further includes the act 1304 of applying a toughening agent. In particular, the act 1304 comprises applying a toughening agent to exterior surfaces of the primary fibers. In some embodiments, the act 1304 comprises applying the toughening agent by spraying the toughening agent onto the exterior surfaces of the primary fibers.

FIG. 13 also illustrates the act 1306 of weaving the primary fibers. In particular, the act 1306 comprises weaving the primary fibers comprising the toughened exterior surfaces to form a secondary fiber comprising interwoven primary fibers. In some embodiments, weaving the primary fibers comprises: feeding the primary fibers through a guide ring; attaching the primary fibers to a fiber braiding machine; and twisting and extending the primary fibers through the guide ring by utilizing the fiber braiding machine.

In some implementations, the series of acts 1300 further comprises an additional act of weaving the secondary fiber with additional secondary fibers to form a tertiary fiber comprising interwoven secondary fibers.

As described, the disclosed method comprises various steps to create a cell-based comestible food product. In some embodiments, the cell-based comestible food product can comprise a plurality of aligned fibers comprising animal cells, wherein each fiber of the aligned fibers exhibits textural variation. Additionally, in some implementations, the plurality of aligned fibers comprises stacked fibers. In some embodiments, an exterior surface of a fiber of the plurality of aligned fibers is tougher than internal material of the fiber. In one or more implementations, the cell-based comestible food product has an external shape of a cut of comestible meat. Furthermore, in some implementations, the external shape is imparted with a mold, stamp, or some combination thereof. In some implementations, the textural variation results from a combination of a harder texture and a softer texture.

The paragraphs above describe methods for forming a cell mass into a cell-based-meat product. FIGS. 14A-14D and the following accompanying paragraphs describe procurement of cells and growth of cells into a cell mass in accordance with one or more embodiments. Generally, FIGS. 14A-14D illustrate a process of collecting cells from an animal, growing cells in a favorable environment, banking successful cells, and collecting cells into a cell mass followed by de-wetting and/or other treatments.

Figure 14A:
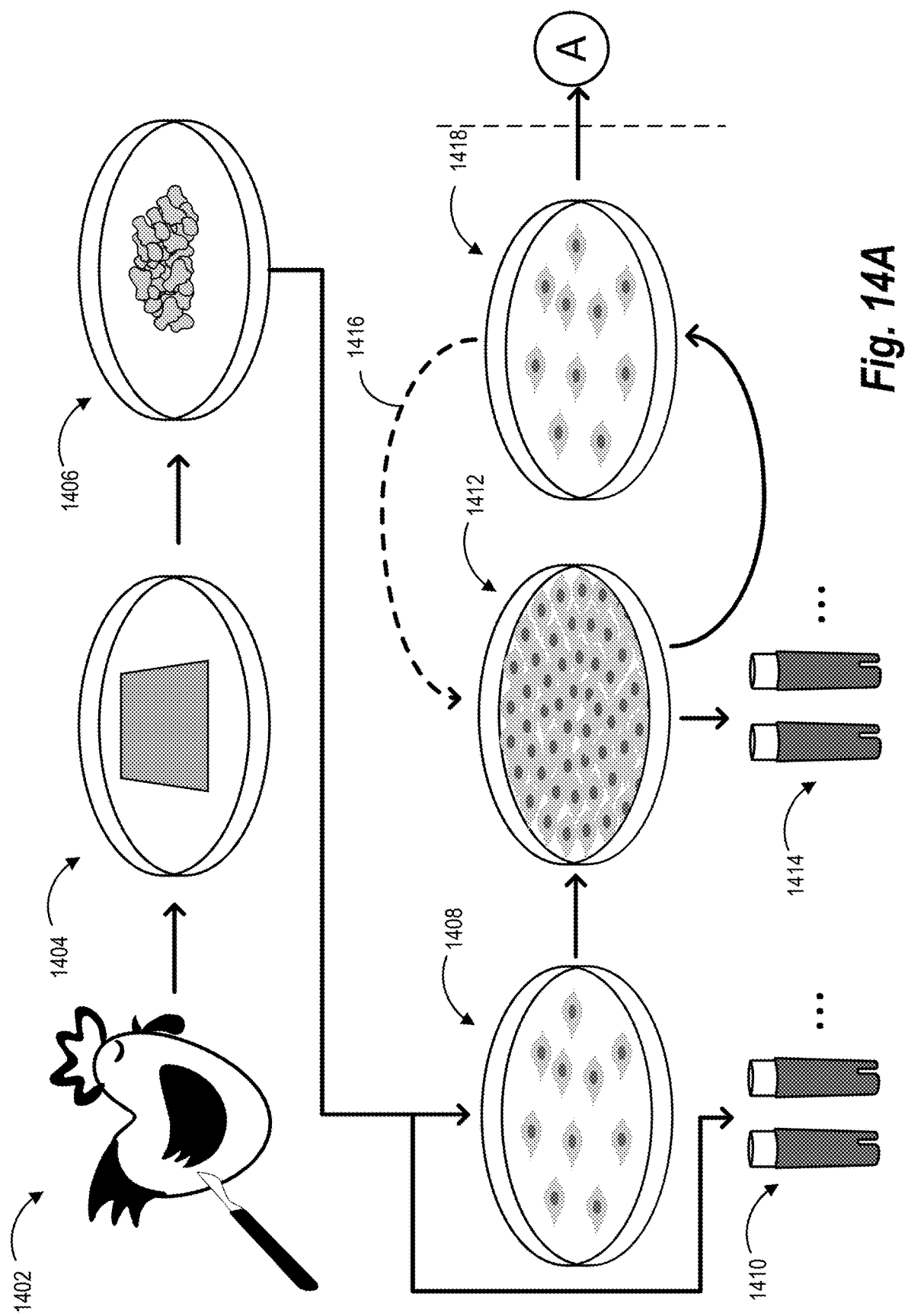
FIGS. 14A-14D illustrate an overview diagram of growing and processing different types of cells in accordance with one or more embodiments of the present disclosure.

As illustrated by step 1402 in FIG. 14A, tissue is collected from a living animal via biopsy. In particular, stem cells, mesenchymal progeny, ectoderm lineage, and/or endoderm lineages can be isolated from the removed tissue. In some implementations of the present disclosure, tissue, such as fat and others, are processed to isolate stem cells, mesenchymal, ectoderm, and/or endoderm progeny or lineage cells. As illustrated, tissue 1404 is removed from an animal. In some examples, the tissue 1404 is removed from a living animal by taking a skin sample from the living animal. For instance, skin or muscle samples may be taken from a chicken, cow, fish, shellfish or another animal.

Cells may be extracted from the tissue 1404 that was removed from the animal. More specifically, the tissue 1404 is broken down by enzymatic and/or mechanical means. To illustrate, FIG. 14A includes digested tissue 1406 that comprises the cells to be grown in cultivation.

Cells in the digested tissue 1406 may be proliferated under appropriate conditions to begin a primary culture. As illustrated in FIG. 14A, cells 1408 from the digested tissue 1406 are spread on a surface or substrate and proliferated until they reach confluence. As shown in FIG. 14A, in some cases, cells 1412 have reached confluence when they start contacting other cells in the vessel, and/or have occupied all the available surface or substrate.

In some examples, cells are stored and frozen (i.e., banked) at different steps along the cell culture process. Cryopreservation generally comprises freezing cells for preservation and long-term storage. In some implementations, tissue and/or cells are removed from a surface or substrate, centrifuged to remove moisture content, and treated with a protective agent for cryopreservation. For example, as part of cryopreservation, tissues and cells are stored at temperatures at or below −80° C. The protective agent may comprise dimethyl sulfoxide (DMSO) or glycerol.

Cells stored through cryopreservation may be used to replenish working cell stock. For instance, while a portion of the digested tissue 1406 is used as the cells 1408 spread on a surface or substrate, the remaining or excess digested tissue 1406 is transferred to cryovials 1410 for storage. Furthermore, the cells 1412 may be banked once reaching confluence and stored in cryovials 1414.

Once the cells 1412 have reached confluence, or just before the cells 1412 have reached confluence (e.g., occupation of about 80% of the substrate), the disclosed process comprises a series of cell passage steps. During cell passage, the cells 1412 are divided into one or more new culture vessels for continued proliferation. To illustrate, the cells 1412 may be diluted or spread on one or more surfaces or substrates to form the cells 1418. The cells 1418 are then grown 1416 to confluence, or just before confluence.

The cycle of dividing the cells 1412 into the cells 1418 for continued proliferation in new culture vessels may be repeated for a determined number of cycles. Typically, cell lines derived from primary cultures have a finite life span. Passaging the cells allows cells with the highest growth capacity to predominate. In one example, cells are passaged for five cycles to meet a desired genotypic and phenotypic uniformity in the cell population.

Figure 14B:
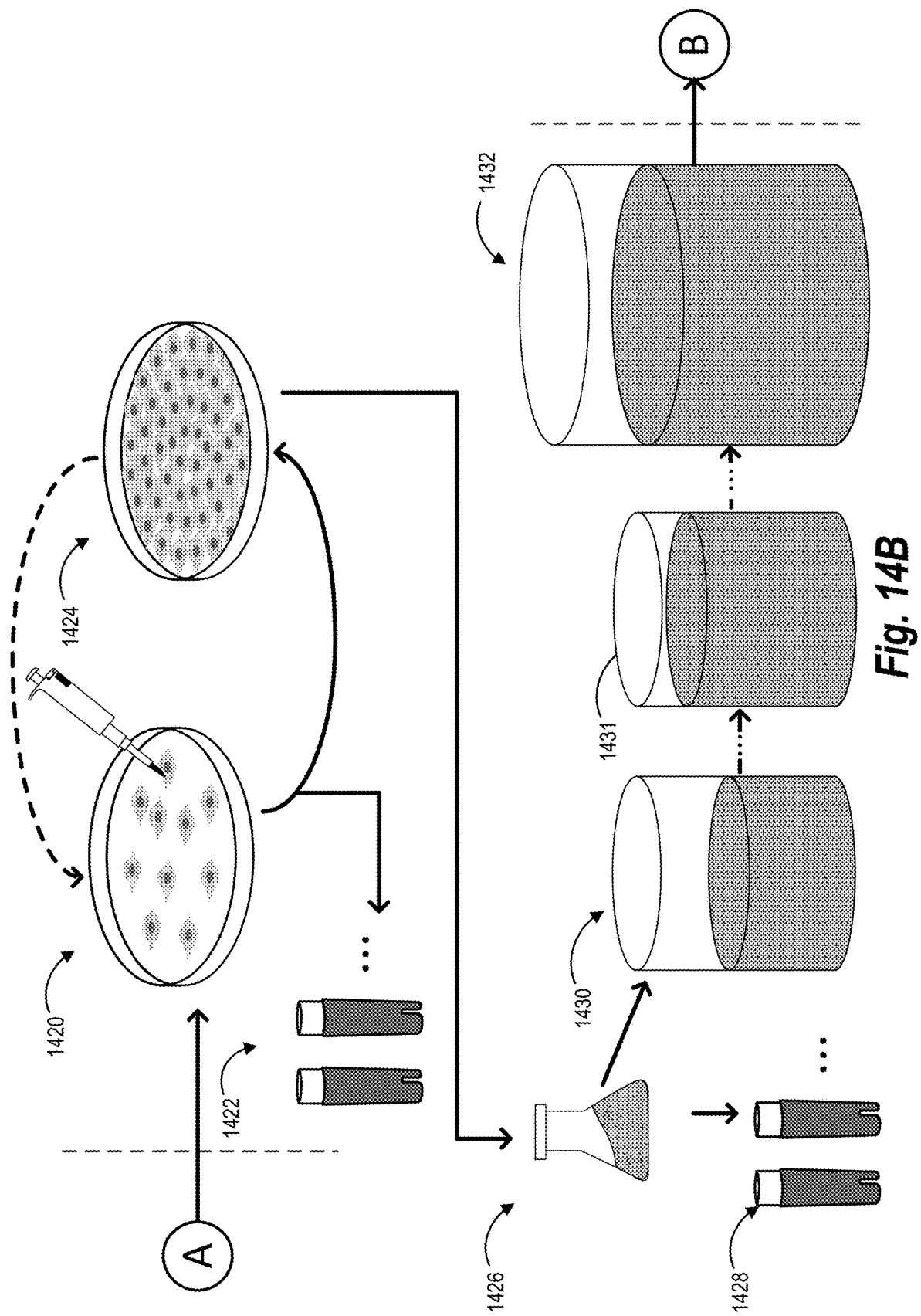

In some implementations, the disclosed method comprises immortalizing cells that have been grown and passaged for the determined number of cycles. For instance, the cells 1418 may be immortalized. As shown in FIG. 14B, cells 1420 have demonstrated a preferred growth capacity to proceed to immortalization. To achieve immortalization, the disclosed process transfects the cells 1420 with genes of interest. In one example telomerase reverse transcriptase (TERT) is introduced to the cells 1420. In some embodiments, the cells may be subjected to a selection process as known by those skilled in the art. The cells 1420 may then be passaged for a predetermined set of passaging cycles. In one example passaging cycle, the cells 1420 are grown to (or near) confluence 1424, then they are reseeded in new growth vessels, preserved in vials 1422, or some combination of both. The disclosed process may include any number of passaging cycles to ensure that the cells have reached immortality (e.g., can passage 60+ times without senescing), a target growth capacity, and/or a target quantity for banking. For example, cells may be passaged until they have reached a passage level of 100 (e.g., have been passaged for 100 passaging cycles). In another example, cells are passaged until they reach a population doubling level of 100.

Cells that have reached immortality or a target growth capacity by living through a target passage level may be adapted to suspension culture. In one example, a suspension culture media and agitation of cells in this suspension environment help cells to adapt and start proliferating in the new growth environment. The cells adapted to suspension 1426 may be stored in cryovials 1428 for cryopreservation and banking. Cells in suspension 1426 will begin to proliferate and the process begins a series of dilute and expand steps.

During dilution and expansion, cells are moved from growth vessels into newer, and progressively larger, growth vessels. For example, cells in suspension 1426 may begin in a single tube. The cells will proliferate and increase in cellular density. Once the cells have reached a target cell number (i.e., viable cell density (VCD) at desired volume), they are diluted and moved to a larger growth vessel. Optionally, the cells are banked in cryovials throughout expansion. For example, once cells in suspension reach a maximum VCD, the cells may begin to leave exponential growth due to overcrowding. After reaching a target density, the suspension cells may be transferred to a larger vessel 1430 and diluted with additional media. The dilute-and-expand steps are repeated using progressively larger vessels (e.g., the vessel 1431 and the vessel 1432) and/or progressive dilution until the cells reach a production-ready volume. For example, cells may be production ready at about a 1,000-100,000 liter scale at 5 million cells per mL. The cells may be banked in cryovials at any of the dilution and expansion cycles.

Figure 14C:
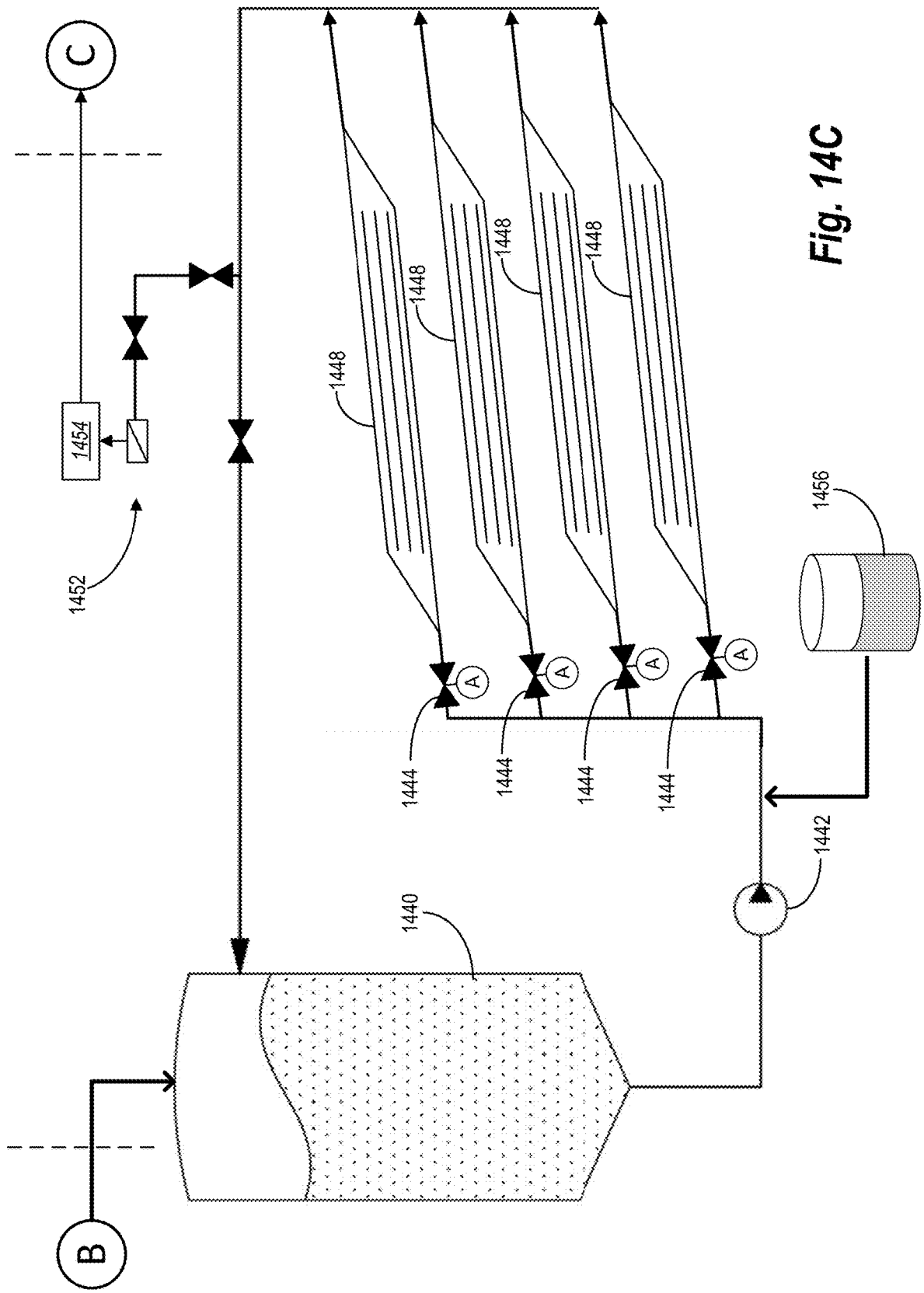

As part of preparing cells to form cell-based-meat products, the disclosed process comprises growing the cells as an adherent culture. Generally, cells that are grown attached to a substrate form a texture that more closely resembles tissue found in conventional meat. Thus, the cells may be transferred from growth in suspension to growth in an adherent reactor. For example, the cells grown in suspension in the vessel 1432 may be transferred to growth on a substrate. FIG. 14C illustrates a bioreactor system comprising a plurality of adherent bioreactors 1448 connecting in parallel to a media vessel 1440. The media vessel 1440 holds the cells grown in suspension media. In some implementations, cells from the vessel 1432 are transferred directly to a cell culture media (or just "media") vessel 1440. In one example, the media vessel 1440 comprises the vessel 1432. The adherent bioreactors 1448 may comprise pipe-based bioreactors. As shown, a plurality of valves 1444 is secured to the plurality of adherent bioreactors 1448 to enable individual use and access of each of the adherent bioreactors 1448. For instance, to limit flow to only a first bioreactor of the plurality of adherent bioreactors 1448, the valve 1444 of the first bioreactor is opened while the remaining valves 1444 are closed. Furthermore, the bioreactor system can include a directional valve 1442 for changing between flow directions.

In some implementations, and as illustrated in FIG. 14C, cells (e.g., adherent cells or suspension adapted cells) are prepared by flowing cells suspended in media (e.g., cell culture media) across substrates in the plurality of adherent bioreactors 1448. More particularly, cells from the media vessel 1440 may contact or land on the substrates in the plurality of adherent bioreactors 1448. Cells and media that flowed through the adherent bioreactors 1448 are cycled back to the media vessel 1440. The media and cells can be cycled through the adherent bioreactors 1448 until a target adherent cell density is reached. For instance, in some implementations, the disclosed method comprises measuring a cell density of outflow from the adherent bioreactors 1448 to infer an adherent cell density.

The cells grow into adherent tissue within the adherent bioreactors 1448. Once they have grown to a target density, either according to a learned timing or according to a measured fluctuation in cell metabolism of components such as glucose and oxygen, then the adherent tissue is ready for removal. The removal process of the disclosed method uses a high-pressure flow to shear the adherent tissue off the substrate surfaces. In one example, wash buffer from a wash tank 1456 is flowed across the substrates in the adherent bioreactors 1448. The wash buffer and cell mixture are flowed through a filter 1452 where the cells are collected into one or more cell masses 1454.

Figure 14D:
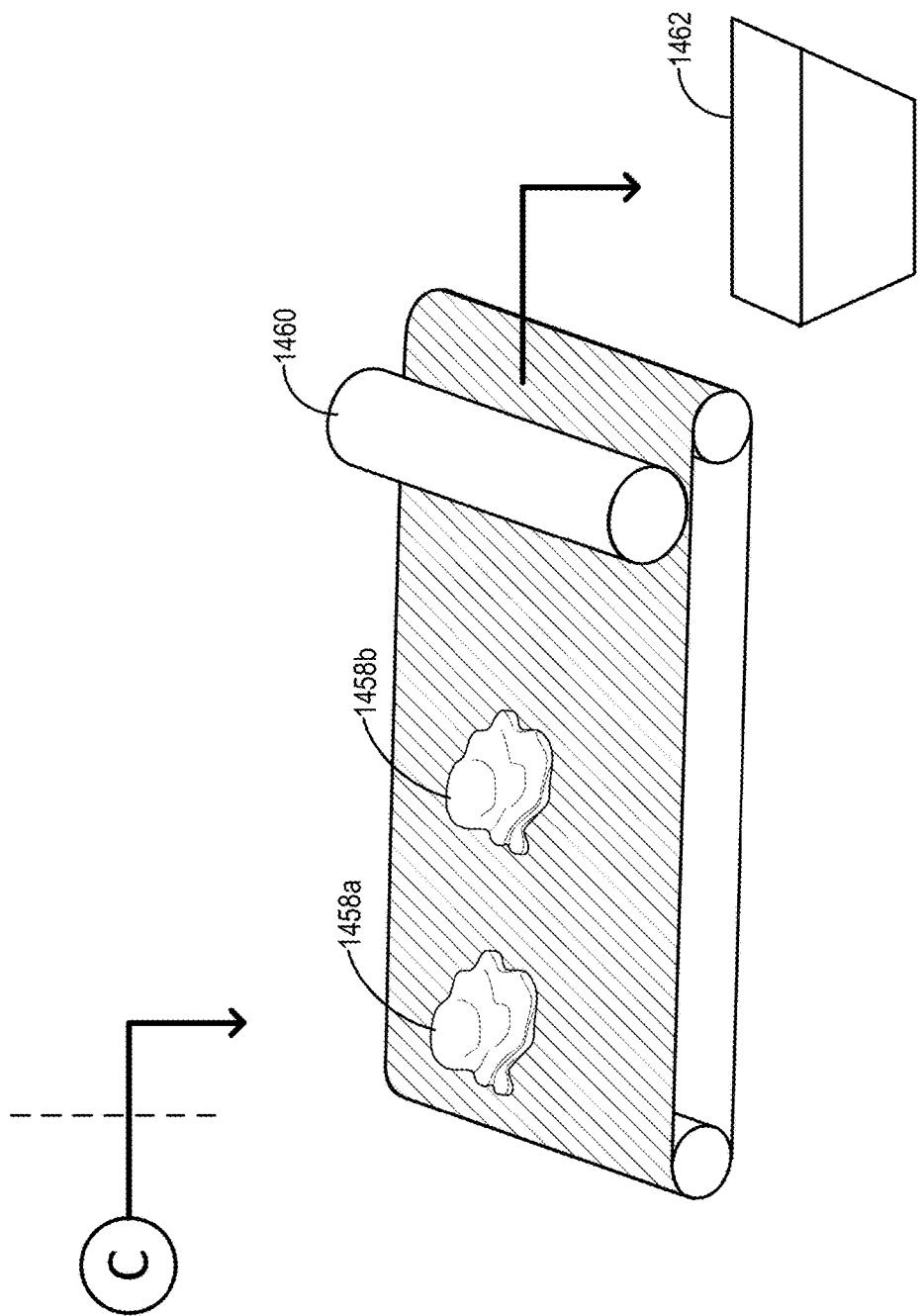

The cell masses 1454 may be further processed to adjust moisture content. FIG. 14D illustrates an example apparatus for reducing moisture content in the cells. In particular, FIG. 14D illustrates a pressure apparatus 1460 that compresses the cell masses 1458a and 1458b. While FIG. 14D illustrates a mechanical method for adjusting moisture content of the cell masses 1458a and 1458b, other methods may be used to adjust moisture content. For example, the cell masses 1458a and 1458b may be mixed with a drying agent, vacuum dried, centrifuged, or otherwise dried. A moisture-adjusted-cell mass may be transferred to a container 1462 for additional processing. For example, the cell mass 1458a or 1458b may be removed from the container 1462 to be formed into a cell-based-meat product.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absent a showing that the terms "first," "second," "third," etc., connote a specific order, these terms should not be understood to connote a specific order. Furthermore, absent a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The present invention may be embodied in other specific forms without departing from its spirit or essential characteristics. Indeed, the described embodiments are to be considered in all respects only as illustrative and not restrictive. For example, the methods described herein may be performed with less or more steps/acts or the steps/acts may be performed in differing orders. Additionally, the steps/acts described herein may be repeated or performed in parallel to one another or in parallel to different instances of the same or similar steps/acts. The scope of the invention is, therefore, indicated by the appended claims rather than by the foregoing description. All changes that come within the meaning and range of equivalency of the claims are to be embraced within their scope.

What is claimed is:

1. A method for forming a cell-based-meat product comprising:
    forming primary structures by filling, with a cell mass comprising cells grown in a reactor, containers having shapes of the primary structures;
    applying a toughening agent to at least a portion of an exterior surface of the primary structures; and
    arranging the primary structures comprising at least partially toughened exterior surfaces to mimic structures in a target slaughtered meat.

2. The method of claim 1, wherein the cell mass comprises cells of a type from at least one of myocytes, adipocytes, or fibroblasts.

3. The method of claim 1, further comprising organizing proto-fibers in the cell mass prior to or during forming the cell mass into the primary structures.

4. The method of claim 1, wherein the primary structures are in the shape of at least one of a primary fiber or a primary sheet.

5. The method of claim 3, wherein the proto-fibers in the cell mass are combed with tines to organize the proto-fibers.

6. The method of claim 3, wherein the containers filled with the cell mass are bent to organize the proto-fibers.

7. The method of claim 1, wherein applying the toughening agent further comprises:
   applying the toughening agent to an interior surface of the containers;
   filling the containers with the cell mass; and
   applying the toughening agent to an exposed surface of the cell mass.

8. The method of claim 1, further comprising:
   removing the primary structures from the containers before spraying the toughening agent on exterior surfaces of the primary structures.

9. The method of claim 1, further comprising:
   removing the primary structures from the containers before immersing the primary structures in a bath comprising the toughening agent.

10. The method of claim 1, wherein the toughening agent comprises at least one of gelatin, gelatin substitutes, carb-based texturizers, food-based tougheners, collagen, or fibroblasts.

11. A method for forming a cell-based-meat product comprising:
   forming a cell mass into primary fibers, wherein the cell mass comprises cells grown in a reactor;
   applying a toughening agent to exterior surfaces of the primary fibers; and
   weaving the primary fibers comprising the toughened exterior surfaces to form a secondary fiber comprising interwoven primary fibers.

12. The method of claim 11, further comprising weaving the secondary fiber with additional secondary fibers to form a tertiary fiber comprising interwoven secondary fibers.

13. The method of claim 11, wherein applying the toughening agent comprises spraying the toughening agent onto the exterior surfaces of the primary fibers.

14. The method of claim 11, further comprising applying a second layer of the toughening agent that at least partially coats the secondary fiber.

15. The method of claim 11, wherein weaving the primary fibers comprises:
   feeding the primary fibers through a guide ring;
   attaching the primary fibers to a fiber braiding machine; and
   twisting and extending the primary fibers through the guide ring by utilizing the fiber braiding machine.

16. The method of claim 4, wherein arranging the primary structures comprises positioning at least one primary fiber at an angle relative to at least one primary sheet.

17. The method of claim 1, wherein the primary structures are arranged to mimic a muscular architecture of a target cut of meat.

18. The method of claim 4, wherein arranging the primary structures comprises positioning a plurality of primary fibers such that at least a portion of lengths of the plurality of primary fibers are parallel.

19. The method of claim 4, wherein arranging the primary structures comprises:
   arranging a primary sheet perpendicular to an interior surface of a mold, wherein the primary sheet mimics fascia connecting a tenderloin and a breast muscle; and
   arranging primary fibers perpendicular to the primary sheet on each side of the primary sheet, wherein:
   a first set of primary fibers on a first side of the primary sheet mimic a shape of the tenderloin; and
   a second set of primary fibers on a second side of the primary sheet mimic a shape of a breast muscle.

20. The method of claim 4, wherein arranging the primary structures to mimic structures in the target slaughtered meat comprises:
   arranging, in a mold, primary sheets of a first cell type mimicking layers of meat; and
   layering, between the primary sheets of the first cell type, primary sheets of a second cell type mimicking layers of fat.

* * * * *